(12) United States Patent
Kjaer et al.

(10) Patent No.: US 11,992,020 B2
(45) Date of Patent: May 28, 2024

(54) DETERMINING MEASURE OF GAPING IN FISH FILLET ITEM

(71) Applicant: MAREL SALMON A/S, Stovring (DK)

(72) Inventors: Anders Kjaer, Stovring (DK); Martin Andersen, Stovring (DK)

(73) Assignee: MAREL SALMON A/S, Stovring (DK)

( * ) Notice: Subject to any disclaimer, the term of this patent is extended or adjusted under 35 U.S.C. 154(b) by 0 days.

(21) Appl. No.: 18/266,652

(22) PCT Filed: Dec. 21, 2021

(86) PCT No.: PCT/EP2021/087017
§ 371 (c)(1),
(2) Date: Jun. 12, 2023

(87) PCT Pub. No.: WO2022/136386
PCT Pub. Date: Jun. 30, 2022

(65) Prior Publication Data
US 2023/0389559 A1     Dec. 7, 2023

(30) Foreign Application Priority Data

Dec. 22, 2020   (EP) .................................. 20216569

(51) Int. Cl.
*A22C 17/00* (2006.01)
*A22C 25/16* (2006.01)
(Continued)

(52) U.S. Cl.
CPC ........ *A22C 17/008* (2013.01); *A22C 17/0086* (2013.01); *A22C 25/16* (2013.01); *G06V 20/64* (2022.01); *G06V 30/18* (2022.01)

(58) Field of Classification Search
CPC ... A22C 17/008; A22C 17/0086; A22C 25/16; G06V 20/64; G06V 30/18
See application file for complete search history.

(56) References Cited

U.S. PATENT DOCUMENTS

| | | | |
|---|---|---|---|
| 2012/0307013 A1 | 12/2012 | Hjalmarsson et al. | |
| 2015/0343000 A1* | 12/2015 | Nordrum | A23K 50/80 424/538 |
| 2020/0077670 A1 | 3/2020 | Hjalmarsson et al. | |

FOREIGN PATENT DOCUMENTS

| | | |
|---|---|---|
| WO | 2020007804 A1 | 1/2020 |
| WO | 2020161229 A1 | 8/2020 |

OTHER PUBLICATIONS

Misimi et al.: "Robust classification approach for segmentation of blood defects in cod fillets based on deep convolutional neural networks and support vector machines and calculation of gripper vectors for robotic processing", Computers and Electronics in Agriculture, vol. 139, May 24, 2017, pp. 138-152.
(Continued)

*Primary Examiner* — John B Strege
(74) *Attorney, Agent, or Firm* — Workman Nydegger

(57) ABSTRACT

A method of determining a measure of gaping in a fish fillet item, involves the steps of obtaining three-dimensional profile data of a first area of the fish fillet item, obtaining optical imaging data of a second area of the fish fillet item, wherein the first area and the second area are overlapping at least within an overlap area; and determining the measure of gaping in the fish fillet item based on the three-dimensional profile data within the overlap area and the optical imaging data within the overlap area.

25 Claims, 11 Drawing Sheets

(51) Int. Cl.
G06V 20/64 (2022.01)
G06V 30/18 (2022.01)

(56) References Cited

OTHER PUBLICATIONS

Balaban et al.: "Quantification of Gaping, Bruising, and Blood Spots in Salmon Fillets Using Image Analysis", Journal of Food Science, vol. 76, No. 3, As Early as Jan. 1, 2011, pp. E291-E297.
Xu et al.: "Computer Vision Detection of Salmon Muscle Gaping Using Convolutional Neural Network Features", Food Analytical Methods, vol. 11, No. 1, Jul. 6, 2017, pp. 34-47.
Merkin et al.: "Digital Image Analysis as a Tool to Quantify Gaping and Morphology in Smoked Salmon Slices," Aquacultural Engineering, vol. 54, As Early as Jan. 1, 2013, pp. 64-71.
International Search Report from corresponding PCT Application No. PCT/EP2021/087017, dated Apr. 7, 2022.
Extended European Search Report from corresponding EP Application No. 20216569.2, dated May 20, 2021.

* cited by examiner

DETERMINING MEASURE OF GAPING IN FISH FILLET ITEM

FIELD OF THE INVENTION

The present invention relates to determining a property of a fish fillet item, and more particularly to a method for determining a measure of gaping in a fish fillet item and a corresponding apparatus, computer program product and use.

BACKGROUND OF THE INVENTION

Fish fillet items may vary in quality and may in particular vary, or suffer quality issues, due to a plurality of quality parameters, such as gaping, which deteriorates quality. Gaping in a fish fillet item may pose limitations to further processing, optionally due to a decrease in structural integrity of the fish fillet item, and/or may lead to downgrading, which may in turn be associated with a decrease in value. Determining a measure of gaping may be beneficial, e.g., with a view to identifying limitations to further processing of a fish fillet item and/or assessing a value of a fish fillet item.

Present methods for determining a measure of gaping may be labour intensive, subjective, and might not be as precise and/or accurate as desirable.

Hence, an improved method for determining a measure of a gaping in a fish fillet item, and a corresponding apparatus, use and computer program product, would be advantageous, and in particular an improved method, apparatus, use and computer program product, enabling determining a measure of gaping in a fish fillet item with reduced labour requirements, which is objective, which has improved precision and/or which has improved accuracy.

SUMMARY OF THE INVENTION

It may be seen as an object of the present invention to provide a method, apparatus, use and computer program product, which overcomes the problems mentioned above. It may be a further object of the present invention to provide an alternative to the prior art. Thus, the above-described object and several other objects are intended to be obtained in a first aspect of the invention by providing a method of determining a measure of gaping in a fish fillet item, the method comprising the steps of:

obtaining three-dimensional (3D) profile data of a first area of the fish fillet item;
obtaining optical imaging data of a second area of the fish fillet item, wherein the first area and the second area are overlapping at least within an overlap area;
determining the measure of gaping in the fish fillet item based on the
i. three-dimensional profile data within the overlap area, and the
ii. optical imaging data within the overlap area.

A possible advantage of the present invention is that it enables automating the method of determining a measure of gaping in a fish fillet item, which may in turn enable reducing labour requirements and/or be objective. For example, each of three-dimensional surface data and optical imaging data can be obtained, e.g., as digital data by means of a processor, and an automated algorithm may process these data and provide in an automated and objective manner the measure of gaping.

Another possible advantage of the invention is that it takes into account both of three-dimensional surface data and optical imaging data, which may in turn enable improving precision and/or accuracy. This may be possible due to the invention taking into account an increased amount of relevant data, where the two types of data may complement each other.

For example, by using both data types, it may be possible in embodiments of the invention, to disregard false positive gaping areas, which appear to be gaping areas according to one data type (such as three-dimensional profile data), but where the other data type (such as optical imaging data) allows ruling out that they are gaping areas.

A false positive gaping area may be caused by, e.g., the presence of one or more foreign objects, such as for a salmon
a foreign object, e.g., any one of:
a piece of plastic, e.g., a piece of plastic having another colour than a salmon (such as being blue or green),
an internal salmon organ (which may be considered a foreign object with respect to the fish fillet item), and
a salmon fish bone (which may be considered a foreign object with respect to the fish fillet item), or
a feature of the fish fillet item, e.g.,
a discoloration, such as a melanin spot or a blood spot.

In another example, by using both data types, it may be possible in embodiments of the invention, to include gaping areas, which in one data type or the other data type would otherwise be a false negative gaping area.

'A measure of gaping' may be understood in the context of any type of measurement scale, such as any one type of nominal, ordinal, interval or ratio. Determining a measure of gaping thus encompasses detection of gaping, such as (qualitatively) determining if, such as whether or not, gaping is present in a fish fillet item. According to a nominal measurement scale, fish fillet items may be categorized, e.g., into two and only two categories, such as the jointly and mutually exclusive categories "gaping" (such as a category for fish fillet items where a level of gaping exceeds a gaping threshold) and "no gaping" (such as a category for fish fillet items where a level of gaping is not exceeding the gaping threshold). A fish fillet item may for example be categorized as gaping if it comprises at least one gaping area, such as a cavity with one or more characteristics (such as a metric defined on the basis of one or more of—or being one of—the following characteristics: optical imaging intensity, colour, volume, area, width, length, depth, largest lateral dimension, angle of largest lateral dimension with respect to a spine direction) exceeding a threshold. According to an ordinal type of measurement scale, fish fillet items may be sorted into ranked groups, e.g., into 3 or 4 or 5 or more groups associated with increased gaping (optionally including a group with little and/or no gaping). According to an interval or ratio type measurement scale, a measure of gaping for a fish fillet item may be quantified, such as given a numerical score, such as said numerical score being objectively calculated based on measured values (e.g., being based on a metric similar to the value of the above-mentioned metric).

A quantified metric may be used for categorization, e.g., lateral dimensions of one or more gaping areas, such as gaping holes, such as the length and/or width of gaping holes in horizontal dimensions for a fish fillet item supported on a horizontal support surface, where 'length' and 'width' are understood as follows: 'Width' being a dimension orthogonal to a spine direction and 'length' being a dimension in a direction parallel with a spine direction. For example, according to one embodiment, a fish fillet item may be categorized in categories 0, (category 1 being non-existent) 2, 3 and 4, as follows:

Category 0: No gaping (where no gaping is optionally understood to include fish fillet items with one or more gaping holes, where gaping hole if present has
A width being
smaller than 0.3 cm, and/or
A length being
smaller than 0.6 cm).

Category 2 (see an example of a fish fillet which may be classified into this category in FIG. 11): Comprises at least one gaping hole with
a width being
equal to or larger than 0.3 cm, and
less than 1.5 cm,
and/or
a length being
equal to or larger than 0.6 cm, and
less than 2.0 cm.

Category 3 (see an example of a fish fillet which may be classified into this category in FIG. 12): Comprises at least one gaping hole with
a width being
equal to or larger than 1.5 cm, and
less than 3.0 cm,
and
A length being
equal to or larger than 2.0 cm.

Category 4 (see an example of a fish fillet which may be classified into this category in FIG. 13): Comprises at least one gaping hole with
a width being
equal to or larger than 3.0 cm,
and
A length being
equal to or larger than 2.0 cm.

In an embodiment, a measure of gaping can be determined fully or partially based on a metric not necessitating identification of one or more (candidate) gaping areas, such as wherein a measure of gaping is based on a measure of roughness, such as a root mean squared (RMS) roughness, of the fish fillet item. For example, the categorization above can be amended to include a category 1 with fish fillets having a certain roughness (and not falling in any one of categories 2 or 3 or 4 (or 5 or 6)).

In each case, the categorization may also include categories 5 and 6, as follows:

Category 5: Comprises at least one gaping hole with
a width being
less than 1.5 cm,
and
a length being
equal to or larger than 2.0 cm.

Category 6: Comprises at least one gaping hole with
a width being
equal to or larger than 1.5 cm,
and
a length being
less than 2.0 cm.

In each categorization, it is understood that a fish fillet item does not qualify for a higher ranking category (e.g., a fish fillet with at least one gaping hole qualifying for category 2 will still only be categorized in category 2 if it comprises no gaping holes qualifying for any one of categories 5, 6, 3 or 4), where categories in different embodiments are ranked in order of (from low to high rank)

0, 2, 3, 4;
0, 1, 2, 3, 4;
0, 2, 5, 6, 3, 4;
0, 1, 2, 5, 6, 3, 4:

'A fish fillet item' is understood as a fish fillet or part thereof (with or without skin, i.e., including deskinned fish filet items), such as a (supreme) cut where a fillet is cut along one or more planes being substantially orthogonal to the spine. 'Fish fillet' may be understood as a cut obtained by slicing substantially parallel, such as parallel, with the spine. It is generally understood that each of three-dimensional profile data and/or the optical imaging data is obtained for a surface of the fish fillet item, which is substantially parallel, such as parallel, with the spine.

'Obtaining' (three-dimensional profile data and/or optical imaging data) may be understood as any one of measuring (such as measuring raw data from which three-dimensional profile data and/or optical imaging data is derived) or receiving (such as receiving previously measured three-dimensional profile data and/or optical imaging data).

'Three-dimensional profile data' may be understood as any type of data (such as spatially resolved in two or three dimensions) comprising information about the three-dimensional profile of the surface of the fish fillet item, where 'three-dimensional profile' is to be understood as the shape of the surface (such as the three-dimensional locations of the parts of the surface) of the fish fillet item. The three-dimensional profile data may be chosen from the following non-limiting set of examples comprising a three-dimensional point cloud, a (rasterized) height map and one or more mathematical functions describing the surface shape, such $z=f(x,y)$, where distance z from a supporting surface is given as a mathematical function $f$ of lateral position (x, y).

"A first area of the fish fillet item' is understood as an area of the fish fillet item, such as the entire surface of the fish fillet item, or a part of the surface visible from a certain direction (e.g., the opposite side of a side facing a supporting surface) or from a point, or a part thereof.

'Optical imaging data' may be understood as data (such as spatially resolved in two or three dimensions) representative of brightness and/or chromaticity, such as observed by a measuring device, such as a scanner (e.g., scanning a point in raster pattern or scanning multiple lines) or an optical camera (e.g., obtaining the optical imaging data in a single snapshot). The optical imaging data may be monochromatic or colour, such as comprising information on red, green and blue (RGB) intensities. By 'optical' is understood that the imaging data is obtained via electromagnetic radiation having wavelengths within the interval [100 nm; 1 mm], such as corresponding to ultraviolet radiation (UV), the spectrum of light visible for man (VIS) and infrared radiation (IR). In a particular embodiment, the imaging data is obtained for electromagnetic radiation within the interval [380 nm; 740 nm], such as corresponding to the spectrum of light visible for man (VIS). 'Optical imaging data' may be understood synonymously and interchangeably with 'optical image data'.

'Data' may generally be understood to be digital data.

'Second area of the fish fillet item' is understood as an area of the fish fillet item, such as the entire surface of the fish fillet item, or a part of the surface visible from a certain direction (e.g., the opposite side of a side facing a supporting surface) or point, or a part thereof.

It is understood that the first area and the second area are at least partially overlapping, such as partially overlapping (such as where the first area is a strict subset of the second area or vice versa or where the overlapping area—the intersection—is a strict subset of both the first area and the second area) or fully overlapping (such as the first and second area being identical to each other, such as where both of the first area and the second area correspond to all parts of the fish fillet item as visible from a certain direction or point).

'Overlap area' is understood as an area occupied by both of the first area and the second area, i.e., an area for which there are both three-dimensional profile data and optical imaging data. It may be understood that the first area and the second are fully overlapping within the overlap area. The overlap area may be coherent or comprise multiple non-coherent (sub-)areas.

"Determining the measure of gaping in the fish fillet item based on the three-dimensional profile data within the overlap area, and the optical imaging data within the overlap area' is understood that the measure of gaping depends on at least each of the three-dimensional profile data within the overlap area and the optical imaging data within the overlap area. It is conceivable and encompassed that the measure of gaping is based on other factors as well.

According to an embodiment the method comprises the step of determining a candidate gaping area set based on the
i. three-dimensional profile data of the fish fillet item; and/or the
ii. optical imaging data of the fish fillet item;
and wherein determining the measure of gaping in the fish fillet item is based on the candidate gaping area set. A possible advantage may be that determining a candidate gaping area set facilitates and/or increases a coupling between one or more areas of gaping and the measure of gaping. Another possible advantage may be that it enables determining a position of one or more gaping areas, which may for example be relevant for subsequent cutting of the fish fillet item, e.g., with a view to cut the fish fillet item, so the at least one or more cuts thereof comprise little or no gaping.

"A candidate gaping area set' may be understood as information identifying one or more areas of the (surface) fish fillet item, where there is or may (with some likelihood) be gaping. It is understood that the 'candidate gaping area set' encompasses both of one or more areas which with some likelihood might (e.g., as determined from solely one of the three-dimensional profile data and the optical imaging data) be gaping areas and a (refined) set of one or more areas which with a higher likelihood, such as with as high likelihood as possible with the method (e.g., as determined from both of the three-dimensional profile data and the optical imaging data), are gaping areas. A 'set' is to be understood as is common in mathematics, such as encompassing a set with a plurality of candidate gaping areas, a single candidate gaping area and no candidate gaping areas (an empty set, which could for example lead to the categorization "no gaping"), i.e., a candidate gaping area set does not imply the presence of a candidate gaping area in the set, let alone a plurality of candidate gaping areas in the set. 'Candidate gaping area set' may furthermore be understood to encompass both a set defining (in a qualitative and/or binary way) if an area (such as corresponding to a pixel) is a gaping area and a set (optionally comprising a plurality of candidate gaping area sub-sets) where (in a quantitative way and/or on a ratio or interval scale) a likelihood of an area being a gaping area.

According to an embodiment there is presented a method wherein determining the measure of gaping in the fish fillet item comprises determining a candidate gaping area set of the fish fillet item, in which each candidate gaping area passes each of:
a test where pass or failure is based on the three-dimensional profile data, such as based exclusively on the three-dimensional profile data, of the fish fillet item; and
a test where pass or failure is based on the optical imaging data, such as based exclusively on the optical imaging data, of the fish fillet item.

A possible advantage is that when each candidate gaping area passes tests based on each of the three-dimensional profile data and the optical imaging data a risk of having one or more false positive candidate gaping areas in the candidate gaping area set is limited, reduced or eliminated. For example, an initial candidate gaping area set can be based on the three-dimensional profile data, and a refined candidate gaping area set can be provided by removing (from the initial candidate gaping area set) one or more false positive candidate gaping areas which do not pass the test based on the optical imaging data.

In an embodiment, the test based on each of the three-dimensional profile data and the optical imaging data is passed only if the candidate gaping area is determined to be a gaping area. In that way only candidate gaping areas which are confirmed to be gaping areas in each modality will be deemed to be gaping areas.

In another embodiment, a candidate gaping areas will be deemed to be a candidate gaping area if it is confirmed to be a gaping area in at least one modality (i.e., based on the three-dimensional profile data and/or the optical imaging data) and if a test based on each of the modalities (i.e., each of the three-dimensional profile data and the optical imaging data) does not result in the candidate gaping area being disproved to be a gaping area. In this embodiment, each candidate gaping area may in each modality be registered as 'confirmed gaping area', 'inconclusive (with respect to gaping area status)' and 'disproved gaping area'. While in a prior embodiment, in order for a candidate gaping area to be deemed a gaping area both modalities would have to register the candidate gaping area as 'confirmed gaping area', this embodiment merely requires that at least one modality registers the candidate gaping area as 'confirmed gaping area' and that a registration according to the other modality is present and either 'confirmed gaping area' or 'inconclusive'. An advantage of this embodiment is that it might serve to include more gaping areas, which would otherwise be false negatives (with respect to an embodiment requiring both modalities to 'actively' confirm the presence of the gaping). In other words, there is presented an embodiment which lowers the bar for when to deem an area to be a gaping area, and more particularly where it is sufficient that one modality finds gaping and the other does not disprove gaping (i.e., not requiring that both modalities confirm gaping).

According to an embodiment there is presented a method wherein determining a candidate gaping area set of the fish fillet item and/or the test where pass or failure is based on the three-dimensional profile data of the fish fillet item comprises comparing:
One or more height values of the three-dimensional profile data of the fish fillet item in a candidate gaping area,
with
One or more height values of the three-dimensional profile data of the fish fillet item in one or more areas adjacent to the candidate gaping area.

A possible advantage may be that it enables identifying and/or testing one or more candidate gaping areas, e.g., by checking if a depth of a candidate gaping area is within a predefined interval of expected depths.

'Adjacent' may generally be understood as a fixed distance or a relative distance, e.g., within a fixed distance (such as within 1, 2, 5, 10 or 20 millimetres) or within a relative distance (such as within a distance corresponding to a smallest dimension of the candidate gaping area) from the border of the candidate gaping area.

According to an embodiment there is presented a method wherein the test where pass or failure is based on the optical imaging data of the fish fillet item comprises comparing:
an actual value of the optical imaging data of the fish fillet item in a position in or adjacent to the candidate gaping area,
with
one or more expected values of the optical imaging data of the fish fillet item in the position in or adjacent to the candidate gaping area.

A possible advantage may be that it enables identifying (and removing from the candidate gaping area set) one or more false positive candidate gaping areas, e.g., where one or more candidate gaping areas have erroneously been identified as such due to a presence of a foreign object, for example due to the presence of a piece of blue plastic (which may have confused an algorithm for identifying an initial set of candidate gaping areas based on the three-dimensional surface profile data), which can be identified by a comparison between the actual value (i.e., plastic blue) and one or more expected values (e.g., a salmon colour, such as a colour within pinkish-orange to light pink, or a colour of fat, such as within white to yellow). Pass or failure may in embodiments be based on a distance from one or more expected values (such as a distance from one or more points value in RGB or the CIE 1931 colour space) relative to a threshold distance or be based on the actual value being identical to one or more expected values (such as within an area in the RGB or CIE 1931 colour space). The one or more expected (salmon) values may be given based on actual fish fillet items, optionally adaptively, e.g., based on (running) average or median colour values of one or more fish fillet items or one or more parts thereof. Alternatively, the one or more expected (salmon) colours may be predetermined, e.g., based on one or more uniquely defined colours, such as sRGB values (r, g, b) of (250, 128, 114), (255, 160, 122), (255, 145, 164) and/or (233, 150, 122), where each sRGB set of values is normalized to [0-255](byte), where the sRGB values are optionally given with reference to IEC 61966-2-1:1999. The predetermined values may alternatively be representative of one or more colours of the 'SalmoFan™ Lineal' available from Koninklijke DSM N.V., Herleen, the Netherlands).

According to an embodiment there is presented a method wherein the test where pass or failure is based on the optical imaging data of the fish fillet item comprises comparing:
an actual value of the optical imaging data of the fish fillet item in a position adjacent to the candidate gaping area,
with
one or more expected values of the optical imaging data of the fish fillet item in the position adjacent to the candidate gaping area.

By such comparison based on a position adjacent to the candidate gaping area, it may be possible to refine the test, such as by taking into account information from the adjacent position, e.g., information on foreign bodies, such as pieces of plastic, etc., which might enable identifying a false positive area.

According to an embodiment there is presented a method wherein the test where pass or failure is based on the three-dimensional profile data of the fish fillet item comprises comparing:
an actual value of the three-dimensional profile data of the fish fillet item in a position adjacent to the candidate gaping area,
with
one or more expected values of the three-dimensional profile data of the fish fillet item in the position adjacent to the candidate gaping area.

By such comparison based on a position adjacent to the candidate gaping area, it may be possible to refine the test, such as by taking into account information from the adjacent position, e.g., information on foreign bodies, such as pieces of plastic, bone structures, etc., which might enable identifying a false positive area.

According to an embodiment there is presented a method wherein determining the measure of gaping in the fish fillet item is based on the candidate gaping area set.

According to an embodiment there is presented a method arranged for allowing, at least under certain circumstances, such as depending on the optical imaging data, that an area of the fish fillet item contributes to the measure of gaping even if it is not considered a gaping area based on the three-dimensional profile data. A possible advantage of this may be that a more precise measure of gaping may be determined, e.g., due to a false negative in the three-dimensional profile data not resulting in underestimation of the measure of gaping.

According to an embodiment there is presented a method arranged for allowing, at least under certain circumstances, such as depending on the optical imaging data, that an area of the fish fillet item does not contribute to the measure of gaping even if it is considered a gaping area based on the three-dimensional profile data. A possible advantage of this may be that a more precise measure of gaping may be determined, e.g., due to a false positive in the three-dimensional profile data not resulting in overestimation of the measure of gaping. In an example, an area is considered a gaping area in the three-dimensional profile data, but due to visible plastic adjacent to the area as observed in the optical imaging data, the area is not taken into account in the determination of the gaping measure due to said area likely not being gaping (e.g., rather being an apparent recess or indentation with respect to the surrounding plastic).

According to an embodiment there is presented a method arranged for allowing, at least under certain circumstances, such as depending on the three-dimensional profile data, that an area of the fish fillet item contributes to the measure of gaping even it is not considered a gaping area based on the optical imaging data. A possible advantage of this may be that a more precise measure of gaping may be determined, e.g., due to a false negative in the optical imaging data does resulting in underestimation of the measure of gaping. For example, in certain lighting conditions, a gaping area may not be visible in the optical imaging data, but can be visible in the three-dimensional profile data, and might thus be included (in particular if no other factors point towards a false positive in the three-dimensional profile data, which may be given priority, e.g., due to three-dimensional profile data all other things equal will be more reliable in the assessment of three-dimensional features, such as gaping areas).

According to an embodiment there is presented a method arranged for allowing, at least under certain circumstances, such as depending on the three-dimensional profile data, that an area of the fish fillet item does not contribute to the measure of gaping even it is considered a gaping area based on the optical imaging data. A possible advantage of this may be that a more precise measure of gaping may be determined, e.g., due to a false positive in the optical imaging data (such as due to a blood spot) not resulting in overestimation of the measure of gaping.

According to an embodiment there is presented a method wherein the measure of gaping is representative of an amount or degree of gaping and/or wherein the measure of gaping is qualified or quantified on a one-dimensional scale, such as exclusively on a one-dimensional scale. The measure of gaping may be understood to be representative of an amount or degree of gaping and/or wherein the measure of gaping is qualified (yes/no) or quantified on a one-dimensional scale, such as exclusively on a one-dimensional scale. The measure of gaping may be based, such as exclusively based, on size and/or number of individual gaping areas and/or a total gaping area, such as wherein the one or more gaping areas and/or the total gaping area are defined by a candidate gaping area set.

According to an embodiment there is presented a method wherein the test based on the optical imaging data of the fish fillet item comprises comparing:
An actual pattern in the optical imaging data of the fish fillet item in a position in or adjacent to the candidate gaping area,
with
an expected pattern of the optical imaging data of the fish fillet item in the position in or adjacent to the candidate gaping area.

A possible advantage may be that it enables identifying (and removing from the candidate gaping area set) one or more false positive candidate gaping areas, e.g., where one or more candidate gaping areas have erroneously been identified as such due to a presence of a foreign object, for example due to the presence of stomach contents (which may have confused an algorithm for identifying an initial set of candidate gaping areas based on the three-dimensional surface profile data), which can be identified by a comparison between an actual pattern (i.e., a noisy pattern of disordered stomach contents) and the expected value (e.g., zebra-like myocommata stripes in salmon).

According to an embodiment there is presented a method wherein the test based on the optical imaging data of the fish fillet item comprises checking for one or more structures of the fish fillet item in a position in or adjacent to the candidate gaping area. A possible advantage may be that it enables identifying (and removing from the candidate gaping area set) one or more false positive candidate gaping areas, e.g., where one or more candidate gaping areas have erroneously been identified as such due to a presence of a structure of the fish fillet item, for example due to the presence of a ridge- and/or valley-like structure at or near the centre fat line (which may have confused an algorithm for identifying an initial set of candidate gaping areas based on the three-dimensional surface profile data), which can be identified in the optical imaging data and taken into account in the test based on the optical imaging data.

According to an embodiment there is presented a method wherein determining the measure of gaping in the fish fillet item comprises simultaneously, and optionally in a non-parallel and/or integrated manner, employing the i. three-dimensional profile data within the overlap area, and the
ii. optical imaging data within the overlap area.

A possible advantage of this embodiment may be that the determination may be faster by simultaneously employing the three-dimensional profile data and the optical imaging data, e.g., as compared to sequentially employing one data type after the other.

In one example an algorithm determines the measure of gaping directly, e.g., via a function, from the three-dimensional profile data and the optical imaging data, such as four-dimensional data comprising both three-dimensional profile data and optical imaging data, such as in the form of a ("4D"-)point cloud where each point is associated with a three-dimensional, spatial vector (such as a vector with three coordinates, e.g., the three cartesian coordinates x, y, and z) and an optical imaging value (such as a monochrome intensity I), such as the combined vectors having the format (x, y, z, I), or six-dimensional data where the monochrome intensity is replaced with RGB colour intensities, such as the six-dimensional data having the format (x, y, z, R, G, B).

In another example, processed data are provided via input from both of the three-dimensional profile data and the optical imaging data, such as the processed data being a derived version of either of the three-dimensional profile data or the optical imaging data where the other data type has been employed to refine details, e.g., where the presence of blue plastic and/or a centre fat line as identified in the optical imaging data have been employed to remove three-dimensional features in the three-dimensional profile data, which are not related to gaping. The derived version of data may comprise data in a non-binary format and/or a format of an interval or ratio type.

"Simultaneously' may be understood that use of three-dimensional profile data within the overlap area and the optical imaging data within the overlap area are at least overlapping such as taking place during identical periods of time, Simultaneous processes are thus not taking place in a sequential manner. 'Non-parallel' may be understood that the processes of employing three-dimensional profile data within the overlap area and the optical imaging data within the overlap area are carried out dependently of each other. 'Integrated' may be understood that the analysis of one or both data types involve the other data type.

According to an embodiment there is presented a method wherein the measure of gaping is determined based on any one of:
a number of candidate gaping areas;
a candidate gaping area ratio between
  i. the total area of the candidate gaping areas, and
  ii. the total area of the fish fillet item;
an average (normalized) depth of the candidate gaping areas;
an area of the candidate gaping areas at a predefined percentile, such as at the $25^{th}$ or $50^{th}$ or $75^{th}$ percentile;
an eccentricity of the candidate gaping areas at a predefined percentile, such as at the $25^{th}$ or $50^{th}$ or $75^{th}$ percentile;
a roughness, such as a root mean squared (RMS) roughness, of the fish fillet item.

According to an embodiment there is presented a method wherein the optical imaging data is optical colour imaging data. A possible advantage may be that optical colour imaging data comprise additional relevant information (relative to optical monochrome imaging data). Optical colour imaging data may be understood as data comprising information about two or more individual wavelengths, such as two or more individual wavelength intervals, such as wavelengths (or wavelength intervals) corresponding to red, green and blue (RGB).

According to an embodiment there is presented a method wherein said measure of gaping is quantitative, such as enabling classifying the fish fillet item into at least 3 or more, such as 4 or more, such as 5 or more, different classes according to the measure of gaping. In embodiments, said measure of gaping is based on an interval or ratio type measurement scale and/or said measure of gaping is given as a numerical score, such as said numerical score being objectively calculated based on measured values.

According to an embodiment there is presented a method wherein the method comprises obtaining, such as measuring,
The three-dimensional profile data; and/or
The optical imaging data;
while the fish fillet item is placed on a non-planar surface. A possible advantage may be that gaping areas may become more pronounced, such as more visible in the three-dimensional profile data and/or the optical imaging data. The non-planar surface may comprise a convex feature, such as an elongated convex feature. In case of an elongated convex feature, a longitudinal axis of the convex feature can be oriented substantially parallel with, such as parallel with, or substantially orthogonal to, such as orthogonal to, a direction of a spine of the fish fillet item. In an embodiment, the method further comprises placing the fish fillet item on a non-planar surface, where the non-planar surface is a conveyor such as a conveyor belt, and conveying the fish fillet item and the non-planar surface comprises a convex feature, such as an elongated convex feature, arranged so that at least a portion of the fish fillet item is bent around an axis being, such as wherein said axis is substantially parallel with, such as parallel with, or substantially orthogonal to, such as orthogonal to, a direction of a spine and/or substantially parallel with, such as parallel with, or substantially orthogonal to, such as orthogonal to, a conveying direction during obtaining, such as measuring, the three-dimensional profile data and/or the optical imaging data. For example, fish fillet items can be conveyed in a direction substantially parallel with a direction of a spine of each fish fillet item and an (optionally elongated and oriented in a direction substantially parallel with the conveying direction) convex feature of the conveyor placed so as to substantially coincide with a fat centreline of the fish fillet items during obtaining, such as measuring, the three-dimensional profile data and/or the optical imaging data. "Longitudinal axis of the elongated feature' may be understood as an axis along the longest dimensions and/or an axis around which there is a minimum moment of inertia. 'Substantially parallel with' may be understood that a smallest angle between two axes, such as an axis along the spine and the longitudinal axis, is equal to or less than 45°, such as less than 45°, such as less than 30°, such as less than 20°, such as less than 10°, such as less than 5°, such as less than 2°, such as less than 1°, such as less wherein said smallest angle is 00). 'Substantially orthogonal to' may be understood that the smallest angle is larger than 45°, such as larger than 60°, such as larger than or 70°, such as larger than 80°, such as larger than 85°, such as larger than 88°, such as larger than 89°, such as wherein said smallest angle is 90°).

When referring to a direction of a spine, it is understood to be a direction of the spine when present or if it had been present, i.e., the absence of a spine in (e.g., a boneless) fish fillet item does not render the direction of a spine meaningless.

According to an embodiment there is presented a method wherein the non-planar surface, such as a conveyor, upon which the fish fillet item, comprises a protrusion having a point being at least 0.5 cm, such as at least 1 cm, such as at least 2 cm, such as at least 3 cm, such as at least 5 cm, away from (such as above) a straight line connecting points on the surface on either side (such as in a conveying direction and/or a direction parallel with a fat centreline or a spine of the fish fillet item) of the protrusion and being within 1 cm to 100 cm from each other, such as within 5 cm to 50 cm, from each other, such as within 10 cm to 25 cm from each other. An advantage of this may be that it makes gaping areas more visible in three-dimensional profile data and/or the optical imaging data.

According to an embodiment there is presented a method wherein the fish fillet item is placed on a protrusion, which protrusion is elongated, such as having an aspect ratio being higher than 1, such as 1.5 or higher, such as 2 or higher, and wherein a smallest angle between a longitudinal axis of the protrusion and an axis of the fish fillet item parallel with a centreline and/or a backbone of the fish had it been present is equal to or smaller than 60°, such as equal to or smaller than 45°, such as equal to or smaller than 30°, such as equal to or smaller than 15°, such as equal to or smaller than 10°, such as equal to or smaller than 5°, such as substantially 0°, such as 0°. An advantage of this may be that it makes gaping areas more visible in three-dimensional profile data and/or the optical imaging data.

According to an embodiment there is presented a method wherein the method is an automated method. An advantage of this may be that a demand of labour is limited, reduced or eliminated. 'Automated method' may be understood a method which requires no human interaction. An automated method may for example be realized using robots and/or processors, optionally operatively coupled with a three-dimensional profile determining device and/or an optical imaging device.

According to an embodiment there is presented a method wherein the method is an in-line method. An advantage of this may be that the method may be efficiently coupled with other methods, which may in turn entail an efficient overall method. 'In-line method' may be understood as a method being part of an overall method where one or more other methods are performed upstream and/or downstream along a line where one or more objects, such as fish fillet items (which may only become fish fillet items along the line, e.g., if fish fillet items are cut from a fish in a method at an upstream station). An in-line method may for example be realized using a conveyor for conveying one or more objects between stations along the line.

It may in general be understood that embodiments of the invention may include a conveyor and/or conveying on a conveyor. 'Conveyor' is generally understood as any means for conveying, such as a conveyor belt, such as an endless conveyor belt and/or a conveyor belt with a load-conveying surface formed by a flat belt (e.g., a flat belt whereupon a fish fillet item is or can be placed).

According to an embodiment there is presented a method wherein the method is an automated and/or inline method.

According to an embodiment there is presented a method wherein said fish fillet item originates from a fish within the order of salmoniformes or gadiformes, such as is an item of any one of trout, salmon, cod and haddock.

According to an embodiment there is presented a method wherein said fish fillet item originates from a fish within the order of salmoniformes, such as is an item of any one of trout and salmon.

According to an embodiment there is presented a method wherein said fish fillet item is a salmon item, such as from a fish within the genus of salmo, such as salmo salar (also known under the common name Atlantic salmon).

According to an embodiment there is presented a method wherein determining the measure of gaping in the fish fillet item comprises determining a candidate gaping area set of the fish fillet item, wherein:

in a step A, determining a candidate gaping area set of the fish fillet item based on at least the three-dimensional profile data of the fish fillet item;

in a step B,
 i. subjecting each candidate gaping area to a test where pass or failure is based on the optical imaging data of the fish fillet item; and
 ii. removing from the set any candidate gaping area failing the test.

A possible advantage of this may be that it provides a simple method for utilizing and benefitting from both types of data. For example, a two-step process can be provided where a step A utilizes the three-dimensional profile data to identify a candidate gaping area set of the fish fillet item, e.g., by means of image segmentation, such as any one of thresholding, edge detection or watershed transformation, and where a step B utilizes the optical imaging data to remove candidate gaping areas from said set, which are determined based on the optical imaging data to be false positives. 'Removing' may be understood as any method yielding a (optionally new) set with the previous elements (candidate gaping areas) except the removed candidate gaping area(s).

According to an embodiment, which is readily combinable with any other embodiment, the method may further comprise one or more pre-processing steps, such as one or more steps changing the raw three-dimensional profile data and/or the raw optical imaging data. A pre-processing step may include one or more of scaling, low-pass filtering, high-pass filtering and band-pass filtering.

According to a further embodiment there is presented a method wherein determining the measure of gaping in the fish fillet item comprises repeating step A and step B until no candidate gaping areas are removed in step B. This may be considered an iterative process. A possible advantage may be that this yields better results (such as in terms of providing a candidate gaping area set with less false positives and/or less false negatives, which may in turn improve the determination of a measure in gaping). For example, a false positive candidate gaping area may be removed the first time step B is carried out (e.g., due to a piece of blue plastic on the fish fillet item), and carrying out step A in a first iteration thereafter may take this removal into account, which may improve identification of (remaining) candidate gaping areas (possibly including one or more candidate gaping areas which was not identified and/or not identified correctly the first time step A was carried out).

According to an embodiment there is presented a method wherein determining the measure of gaping in the fish fillet item comprises:

Determining, optionally based on the three-dimensional profile data, a candidate gaping area set of the fish fillet item;

Reducing, optionally based on the three-dimensional profile data, the candidate gaping area set of the fish fillet item by:

i. Classifying each candidate gaping area in the candidate gaping area set as weak or strong,
 ii. Removing one or more weak candidate gaping areas, which are not connected to strong candidate gaping areas, from the candidate gaping area set of the fish fillet item.

A possible advantage of this may be that it reduces a risk of having false positive candidate gaping areas in the (resulting) candidate gaping area set. Distinguishing between weak or strong candidate gaping areas can be done, e.g., by thresholding such as with respect to noise level, depth, area or a dimension of the candidate gaping area in a direction with respect to a direction orthogonal to a direction of a spine.

According to an embodiment there is presented a method wherein each of:

The three-dimensional profile data; and
The optical imaging data;

Are spatially resolved in two dimensions. 'Spatially resolved in two dimensions' is understood that a value (such as spatial coordinate in certain dimension, such as the 'z'-dimension, or a colour or monochrome intensity) is provided for a plurality of spatial locations distributed in at least two linearly independent directions (such as linearly independent with respect to each other and/or the value), such as is the case for images, three-dimensional point clouds (where z-values is provided for corresponding distributed x- and y-values) and height maps (where z-values are provided for rasterized, distributed x- and y-values).

According to an embodiment there is presented a method wherein the three-dimensional profile data is processed, such as pre-processed, by subtracting a blurred version of the three-dimensional profile data from the three-dimensional profile data. A possible advantage of this may be that it enables flattening the three-dimensional profile data while maintaining the information about the gaping areas and/or subtracting the overall shape of the fish fillet item, which may in turn facilitate an improved identification of the candidate gaping areas. In a further embodiment, this process is carried out iteratively, which may improve the resulting three-dimensional profile data, such as improve the three-dimensional profile data in one or more regions at or near edges of the fish fillet item.

According to an embodiment there is presented a method, wherein the method further comprises determining one or more positions of one or more candidate gaping areas of the fish fillet item on the basis of at least the i. three-dimensional profile data of the fish fillet item; and the
 ii. optical imaging data of the fish fillet item.

A possible advantage may be that determining said one or more positions enables providing (feeding back) relevant information to upstream processing stations. For example, a need for adjusting processing at an upstream processing station with a view to reduce gaping may depend on the positions of the candidate gaping areas. Another possible advantage may be that determining said one or more positions enables providing relevant information to downstream processing stations. For example, any one of cutting, sorting, grading, and processing may depend (not only on the presence of candidate gaping areas, but also on) the one or more positions of one or more candidate gaping areas.

According to an embodiment there is presented a method, wherein the method further comprises determining a distribution of fish fillet item portion cuts over the fish fillet item dividing the fish fillet item into fish fillet item portions on the basis of at least the determined one or more positions of the one or more candidate gaping areas and at least one fish portion feature.

A possible advantage may be that the fish fillet item may subsequently be cut into fish fillet item portions based also on the location of candidate gaping areas in the food item and/or that the number of fish fillet item portions containing candidate gaping areas may be reduced. This is because the cutting device controlled in this manner is effectively able to cut out areas containing candidate gaping areas.

A possible advantage may be that the method enables increasing the applicability of the fish fillet item or parts thereof, such as taking as input a fish fillet item with a certain grading (such as a relatively bad grading due to gaping) and outputting cut fish fillet sub-items (where fish fillet sub-item is understood to encompass each of a sub-item of an entire fish fillet and a sub-item of a fish fillet item, such as a fish fillet item sub-item) of an equal or worse grading and cut fish fillet sub-items of a better grading, where the applicability and/or value of the fish fillet sub-items with better grading alone or together with the remaining fish fillet sub-items presents an improved applicability and/or value compared to the fish fillet items of the (initial) certain grading. For example, a fish fillet item may have a (poor) grading entailing one or more of low value, an export restriction, limited applicability (e.g., because the presence of gaping means it cannot be sliced), yet upon cutting according to a clever distribution of fish fillet item portions cuts, the resulting fish fillet sub-items may, e.g., have higher value, e.g., due to higher grading for some portions cuts entailing a higher averaged value of all the fish fillet sub-items, or enable exporting some of the fish fillet sub-items, or allowing use of some of the fish fillet sub-items for purposes for which the fish fillet item was not applicable.

According to a further embodiment there is presented a method, wherein the at least one fish fillet item portion feature is selected from the group of: portion size, portion weight, portion shape, portion colour, portion colour distribution, portion meat texture and/or portion meat-fat ratio.

According to an embodiment there is presented a method, wherein the method further comprises cutting the fish fillet item into fish fillet item portions according to the determined distribution of fish fillet item portion cuts. A possible advantage may be that it can be avoided that cutting of the fish fillet item is carried out without taking account of the positions of the candidate gaping areas (which would have entailed a risk of cutting the fish fillet item in a candidate gaping area thereby creating two cut fish fillet item portions containing candidate gaping areas). Accordingly, embodiments of the invention allow for optimised yield of cut fish fillet item portions. When cutting close to a candidate gaping area in a leading part and also close to the rear part of a candidate gaping area, such as cutting across a fish fillet item similar to performing a portion cut, such a part with a candidate gaping area may look like a fish fillet item portion and being a 'candidate gaping area-containing portion', though preferably it is sorted out, and may be used for other purposes such as minced meat.

According to a further embodiment there is presented a method, wherein the method further comprises sorting the fish fillet item and/or one or more portion cuts of the fish fillet item based on the measure of gaping in the fish fillet item and/or the one or more portion cuts of the fish fillet item. In some embodiments, the method comprises a step of sorting the fish fillet item and/or the cut food item portions, wherein the sorting is based at least on the measure of gaping, such as the measure of gaping of the (entire) fish fillet item portion and/or a measure of gaping specific to each portion cut of the fish fillet item (for example wherein said specific measure may also be based on the one or more positions of one or more candidate gaping areas of the fish fillet item, e.g., if/which candidate gaping areas are present in a portion cut).

According to a further embodiment there is presented a method, wherein the method further comprises providing, such as feeding back, a parameter based on the measure of gaping to an upstream station and/or to a downstream station, such as adjusting processing at an upstream station and/or at a downstream station based on said parameter. A possible advantage may be that this enables improving or optimizing processing and/or the conditions of the living fish.

For example, in case a measure of gaping increases and/or exceeds a threshold, providing a parameter based on the measure of gaping to an upstream station may allow adjusting processing at the upstream station so as to limit, reduce or eliminate the increase in the measure of gaping and/or keep the measure of gaping below said threshold.

In another example, in case a measure of gaping is provided to a downstream station, said measure may allow (determining a route of) processing, sorting and/or grading based on the measure of gaping.

A possible advantage of sorting may be that—in analogy with the advantages referred to above for a method comprising determining a distribution of fish fillet item portion cuts—is that it enables increasing the applicability of a plurality of fish fillet items, such as taking as input a plurality of fish fillet items where the plurality of fish fillet items is associated with a certain grading (such as a relatively bad grading due to, e.g., an actual average gaping or a risk of a certain gaping of any fish fillet item) and outputting a sub-set of fish fillet items of an equal or worse grading and another subset of fish fillet items of a better grading, where the applicability and/or value of the subset of fish fillet items with better grading alone or together with the remaining fish fillet items presents an improved applicability and/or value compared to the plurality of fish fillet items of the (initial) certain grading. For example, a plurality of fish fillet items may have a (poor) grading entailing one or more of low value, an export restriction, limited applicability (e.g., because the presence of gaping means it cannot be sliced), yet upon sorting the fish fillet items according to a measure of gaping the resulting subsets of fish fillet items may, e.g., have higher value, e.g., due to higher grading for fish fillet items within one or more subsets of fish fillet items entailing a higher averaged value of all the fish fillet items, or enable exporting some of the fish fillet items, or allowing use of some of the fish fillet items for purposes for which the plurality of fish fillet items was not applicable.

According to a second aspect of the invention, there is presented a fish fillet item processing apparatus for determining a measure of gaping in a fish fillet item comprising:
  a three-dimensional profile determining device, such as a camera and a line laser, for generating three-dimensional profile data of a first area of the fish fillet item;
  an optical imaging device, such as a camera, for generating optical imaging data of a second area of the fish fillet item, wherein the second area is at least partially overlapping with the first area; and
  a processing unit, such as a computer, operatively coupled to the three-dimensional profile determining device and the optical imaging device and arranged for carrying out the method of the first aspect.

A 'three-dimensional profile determining device' may be understood as any device capable of determining, such as measuring, three-dimensional profile data for a fish fillet item, such as based on contact or non-contact methods, for example a 3D laser line profile sensors, e.g., based on a line laser with a line projected onto the fish fillet item and moved relative to the fish fillet item in a direction non-parallel, such as orthogonal to, the laser line direction (e.g., due to the fish fillet item being conveyed), or a point laser being scanned in a raster pattern across the fish fillet item.

'An optical imaging device' may be understood as any device capable of determining, such as measuring, optical imaging data for a fish fillet item. The optical imaging device may obtain all parts of the optical imaging data simultaneously (e.g., as a snapshot) or at different points in time (such as scanning line-by-line). The optical imaging device may comprise a light source. The optical imaging device may be any one of a (digital) camera or a (digital) scanner.

According to an embodiment there is presented a fish fillet item processing apparatus wherein the apparatus is further comprising a conveyor, such as a conveyor belt, for conveying the fish fillet item, such as for conveying the fish fillet item to and/or away from the three-dimensional profile determining device and/or the optical imaging device. The conveyor may comprise an in-feed conveyor conveying the fish fillet item past the optical imaging device and optionally towards a cutting device. The at least one conveyor may further comprise an out-feed conveyor arranged to convey the cut fish fillet item portion optionally away from the cutting device. The in-feed conveyor and out-feed conveyor may be arranged in an end-to-end arrangement defining a cutting plane there between, the cutting device being arranged to cut the fish fillet item in the cutting plane.

Also, the apparatus may further comprise a sorting device arranged downstream of the three-dimensional profile determining device and the optical imaging device where the processing unit is arranged for sorting the fish fillet items based on the measure of gaping.

Also, the apparatus may further comprise a cutting device arranged downstream of the three-dimensional profile determining device and the optical imaging device, wherein the controller is configured to control the cutting apparatus based at least on the determined distribution of portion cuts and/or the determined location of defective areas. This has the further advantage that the cutting apparatus need not itself comprise means for locating candidate gaping areas as this information is already available in the processing unit.

Optionally, the sorting device is arranged downstream of the cutting device and the processing unit is configured to control the sorting apparatus, e.g., based at least on the determined distribution of portion cuts and the determined location of the candidate gaping areas for effective and automated sorting of the cut fish fillet item portions. This has the further advantage that the sorting apparatus need not itself comprise means for locating candidate gaping areas as this information is already available in the processing unit.

According to a third aspect of the invention, there is presented a computer program, such as a computer program product, comprising instructions which, when the program is executed by a computer, cause the computer to carry out the method of the first aspect and/or comprising instructions to cause the apparatus of the second aspect to execute the steps of the method of the first aspect.

According to a fourth aspect of the invention, there is presented use of a fish fillet item processing apparatus, such as the fish fillet item processing apparatus according to the second aspect, or a computer program, such as a computer program product, such as the computer program or computer program product according to the third aspect, for performing the method of the first aspect.

According to a further aspect, there is presented a computer-readable medium having stored thereon the computer program, such as the computer program product, of the third aspect.

The first, second, third and fourth aspect of the present invention may each be combined with any of the other aspects. These and other aspects of the invention will be apparent from and elucidated with reference to the embodiments described hereinafter.

BRIEF DESCRIPTION OF THE FIGURES

The method, apparatus, computer program product and use of an apparatus or computer program product for determining a measure of gaping in a fish fillet item according to the invention will now be described in more detail with regard to the accompanying figures. The figures show one way of implementing the present invention and is not to be construed as being limiting to other possible embodiments falling within the scope of the attached claim set.

DETAILED DISCLOSURE OF THE INVENTION

Figure 1:
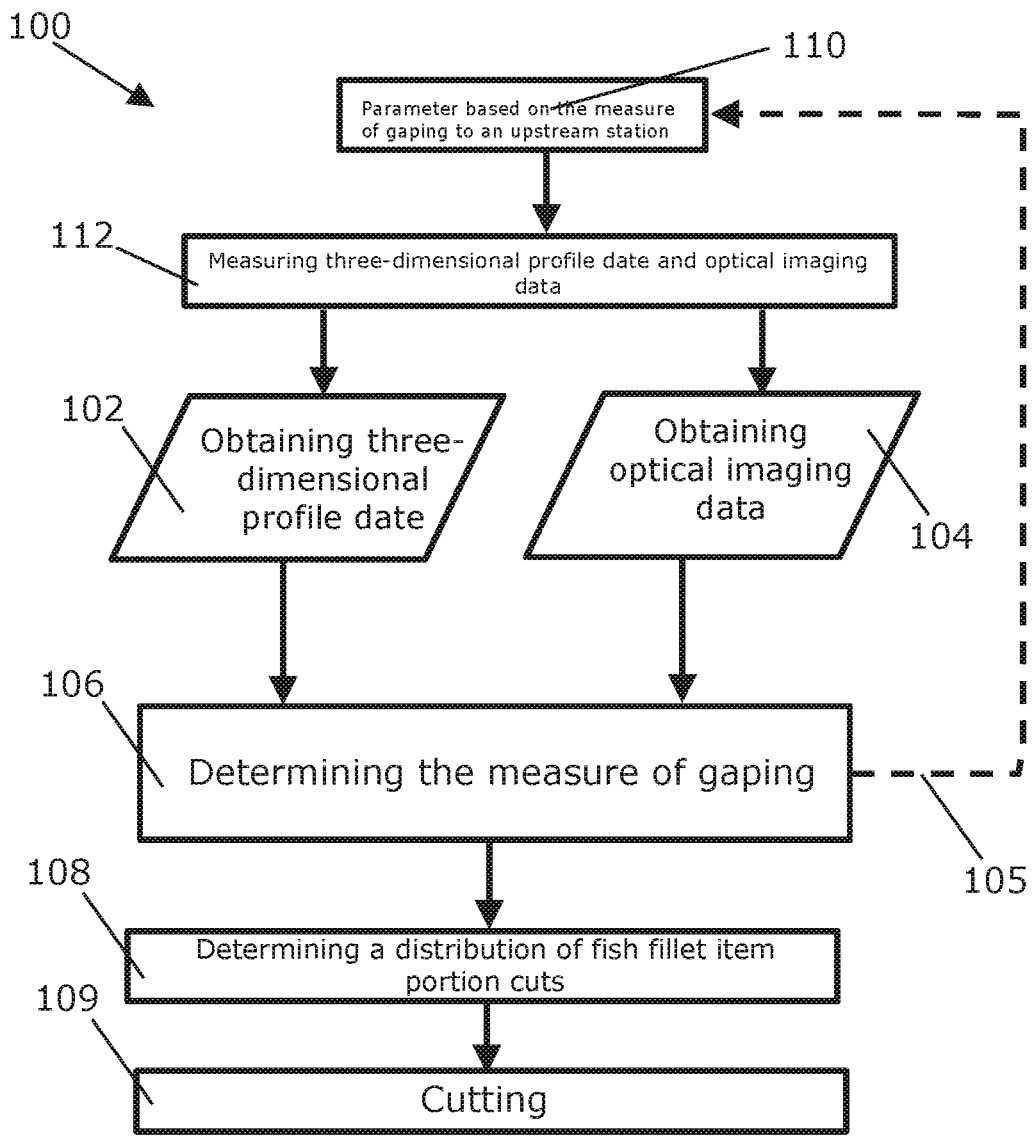
FIG. 1 shows a flow-chart illustrating a method of determining a measure of gaping in a fish fillet item.

FIG. 1 shows a flow-chart illustrating a method 100 of determining a measure of gaping in a fish fillet item, which in FIG. 1 is a salmo salar (Atlantic salmon) species, the method comprising the steps of:
  Obtaining 102 three-dimensional profile data of a first area of the fish fillet item;
  Obtaining 104 optical imaging data of a second area of the fish fillet item, wherein the first area and the second area are overlapping at least within an overlap area;
  determining 106 the measure of gaping in the fish fillet item based on the
    i. three-dimensional profile data within the overlap area, and the
    ii. optical imaging data within the overlap area.

The method 100 shown in FIG. 1 furthermore comprises providing 105 a parameter based on the measure of gaping to an upstream station 110, such as a thawing or de-freezing station, so that operation can be assessed, such as adjusted and/or improved, in case the measure of gaping could or should be improved. The figure also shows a step of measuring 112 three-dimensional profile data and optical imaging data, and in this embodiment the steps of obtaining 102 three-dimensional profile data and obtaining 104 optical imaging data is realized by receiving previously measured three-dimensional profile data and/or optical imaging data.

In the specific embodiment depicted in FIG. 1, the method further comprises (such as for example within the step of determining 106 the measure of gaping) determining one or more positions of one or more candidate gaping areas of the fish fillet item on the basis of at least the colour imaging data of the fish fillet item; and the three-dimensional profile data of the fish fillet item. The figure also shows determining 108 a distribution of fish fillet item portion cuts over the fish fillet item dividing the fish fillet item into fish fillet item portions on the basis of at least the determined one or more positions of the one or more candidate gaping areas and at least one fish portion feature.

The step of obtaining 102, 104 the two types of data, determining 106 the measure of gaping and determining 108 a distribution of fish fillet item portion cuts might be carried out on the same processing unit, such as in the same algorithm.

FIG. 1 furthermore shows sending the distribution of fish fillet item portion cuts to a downstream (cutting) station, where it can be used for cutting 109.

Figure 2:
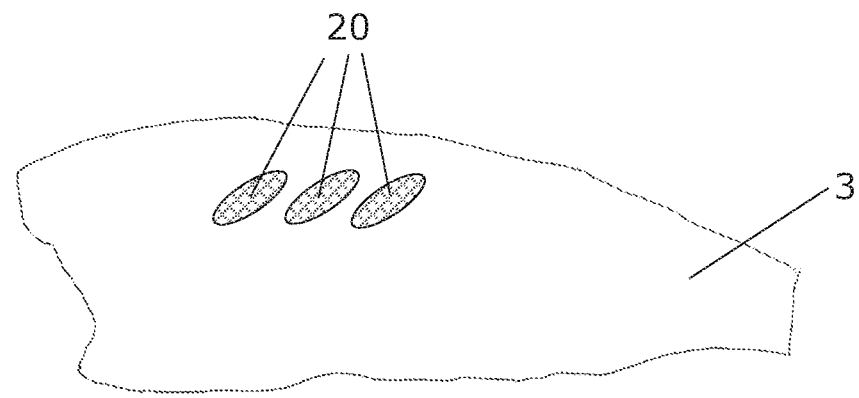
FIG. 2 shows a fish fillet item associated with a candidate gaping area set.

FIG. 2 shows a fish fillet item 3 associated with a candidate gaping area set, which in the figure comprises three candidate areas 20 of gaping. The specific candidate area set in FIG. 2 is representative of actual (true) gaping areas of the specific fish fillet item 3.

Figure 3:
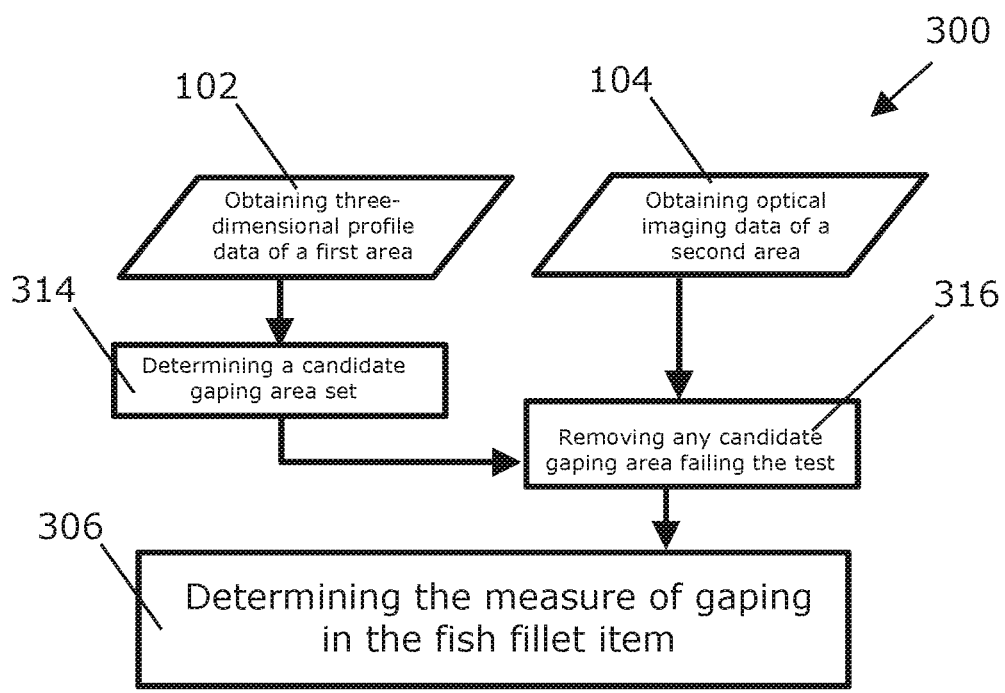
FIG. 3 shows a flow-chart of a method of determining a measure of gaping in a fish fillet item.

FIG. 3 shows a flow-chart of a method 300 of determining a measure of gaping in a fish fillet item, wherein the method comprises the steps of
  obtaining 102 three-dimensional profile data of a first area of the fish fillet item;
  obtaining 104 optical imaging data of a second area of the fish fillet item, wherein the first area and the second area are overlapping at least within an overlap area;
and additionally comprises the step of:
  determining a candidate gaping area set based on the
    i. three-dimensional profile data of the fish fillet item; and/or the
    ii. optical imaging data of the fish fillet item;
and wherein determining 306 the measure of gaping in the fish fillet item is based on the candidate gaping area set, and more particularly in the specific method of FIG. 3 this comprises determining a candidate gaping area set of the fish fillet item, wherein:
  in a step A, determining 314 a candidate gaping area set, such as an initial candidate gaping area set, of the fish fillet item based on at least the three-dimensional profile data of the fish fillet item;
  in a step B,
    i. subjecting each candidate gaping area to a test where pass or failure is based on the optical imaging data of the fish fillet item; and
    ii. removing 316 from the set any candidate gaping area failing the test, such as thereby providing a revised candidate gaping area set,
and determining 306 the measure of gaping in the fish fillet item based on the (revised) candidate gaping area set with areas removed.

Figure 4:
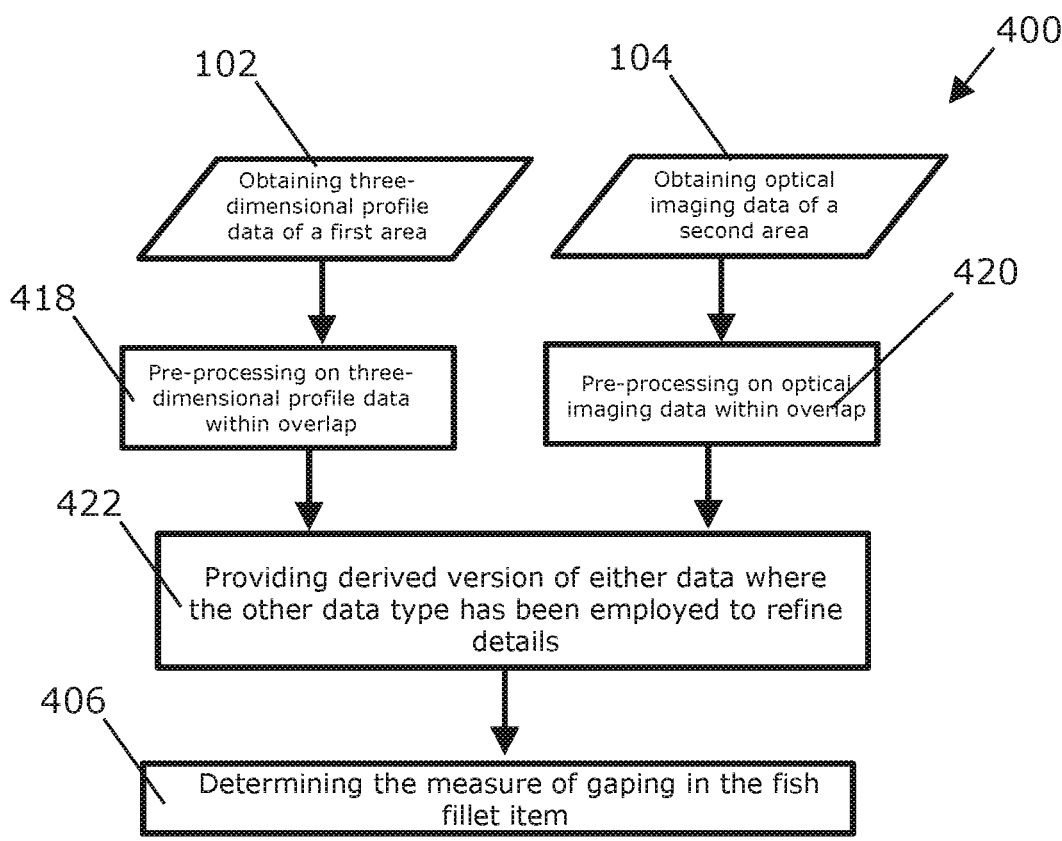
FIG. 4 shows a flow-chart of a method.

FIG. 4 shows a flow-chart of a method 400 comprising the steps of
  obtaining 102 three-dimensional profile data of a first area of the fish fillet item;
  obtaining 104 optical imaging data of a second area of the fish fillet item, wherein the first area and the second area are overlapping at least within an overlap area;
and wherein the method comprises simultaneously employing the
  i. three-dimensional profile data within the overlap area, and the
  ii. optical imaging data within the overlap area.

The figure furthermore shows pre-processing being carried out 418 on the three-dimensional profile data within the overlap area and carried out 420 on the optical imaging data within the overlap area. Simultaneously employing the two data types may be realized by providing 422 a derived version of either of the three-dimensional profile data or the optical imaging data where the other data type has been employed to refine details, such as wherein the derived version of data may comprise data in a non-binary format and/or a format of an interval or ratio type. The method can then comprise determining 406 the measure of gaping in the fish fillet item based on derived version of the data, i.e., simultaneously based on both data types.

In an alternative embodiment, there is provided a function, such as G(input)=(measure of gaping), which takes an input and directly converts it to a measure of gaping, wherein the input may be a set of data (such as a vector), comprising spatial coordinates (x, y, z) and/or image data, such as monochrome intensity (I) or colour values (e.g., R, G, B). 'Directly' may be understood that no intermediate steps, such as generation of initial candidate gaping area set, are created.

Figure 5:
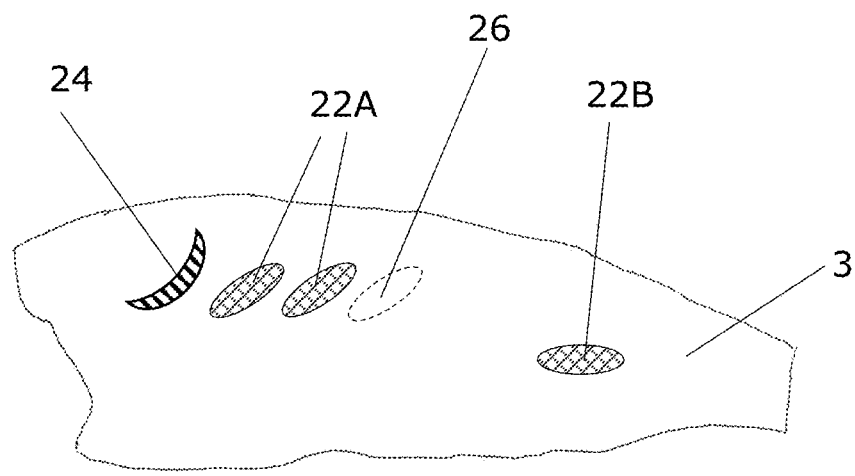
FIG. 5 shows a candidate gaping area set based on the optical imaging data.
Figure 6:
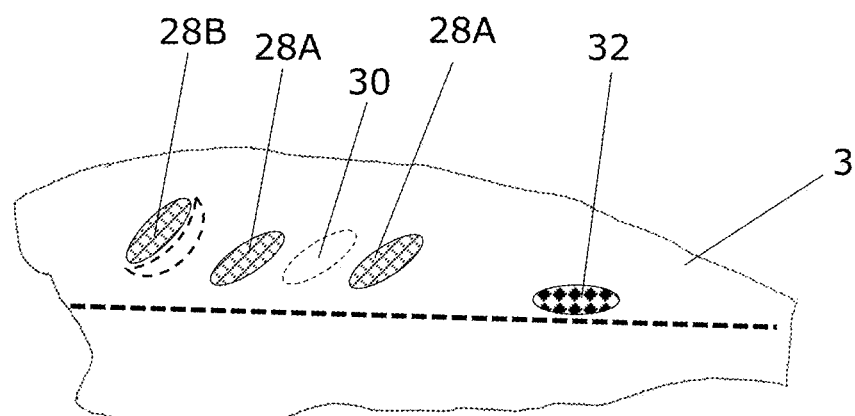
FIG. 6 shows a candidate gaping area set based on the three-dimensional profile data.

FIG. 5-6 illustrates results from independently generating candidate gaping area sets from either of the three-dimensional profile data of the fish fillet item (FIG. 5) and/or the optical imaging data of the fish fillet item (FIG. 6), wherein the fish fillet item 3 is the same as depicted in FIG. 2 (where FIG. 2 comprises a true candidate gaping area set).

FIG. 5 shows that the candidate gaping area set based on the optical imaging data correctly comprises gaping areas 22A. However, a true gaping area is missing as indicated by the area 26 encircled by a dashed ellipse. Furthermore, a false positive gaping area 22B is also included. Furthermore, the figure shows a piece of crescent moon shaped blue (plastic) area 24.

FIG. 6 shows that the candidate gaping area set based on the three-dimensional profile data correctly comprises gaping areas 28A. However, a true gaping area is missing as indicated by the area 30 encircled by a dashed ellipse. Furthermore, a false positive gaping area 28B is also included. Furthermore, the figure shows a cavity 32 adjacent to a centre line indicated with the thick, dashed line.

FIGS. 5-6 show that neither data modality yields a correct candidate gaping area set since each modality comprises both a false negative and a false positive candidate gaping area. However, by utilizing both data types an improved, or even true, candidate gaping area set can be achieved. For example, an initial candidate gaping area set can be provided by including all candidate gaping areas of each modality, and then optionally removing some of the candidate gaping areas in one or both modalities based on information from the other modality. For example, the candidate gaping area 22B in FIG. 5 can be removed because it is too close to the centre line as observed in FIG. 6 and oriented with major axis parallel to the centre line and hence very likely a false positive in FIG. 6. Similarly, the candidate gaping area 28B in FIG. 6 can be removed because it is too close to crescent moon shaped blue (plastic) area 24 and hence very likely a false positive in FIG. 6. The candidate gaping areas in area 26 in FIG. 5 and area 30 in FIG. 6 are included because there might be no reason for removing them and they are hence considered false negative in the modalities where they are not included in the candidate gaping area set. Hence, the result might be that even though each modality is wrong in several ways (false positives and false negatives), by combining the modalities an improved measure of gaping can be achieved, optionally via an improved candidate gaping area set.

The candidate gaping area 28B in FIG. 6 may be considered a false positive because due to failing a test, wherein the test where pass or failure is based on the optical imaging data (cf., FIG. 5) of the fish fillet item comprises comparing:
  an actual value (such as "blue") of the optical imaging data of the fish fillet item in a position in or adjacent to the candidate gaping area,
with
  one or more expected values (such as salmon coloured) of the optical imaging data of the fish fillet item in the position in or adjacent to the candidate gaping area
wherein the comparison might for example comprise checking if a colour channel, such as the blue "B" channel in a set of red-green-blue (RGB) channels, exceeds a threshold value.

In another approach a revised candidate gaping area set of the fish fillet item may be provided wherein only candidate gaping areas identified in both modalities are included, such as wherein each candidate gaping area in the revised candidate gaping area set passes each of:
  a test where pass or failure is based on the three-dimensional profile data, such as based exclusively on the three-dimensional profile data, of the fish fillet item; and
  a test where pass or failure is based on the optical imaging data, such as based exclusively on the optical imaging data, of the fish fillet item.

Figure 7:
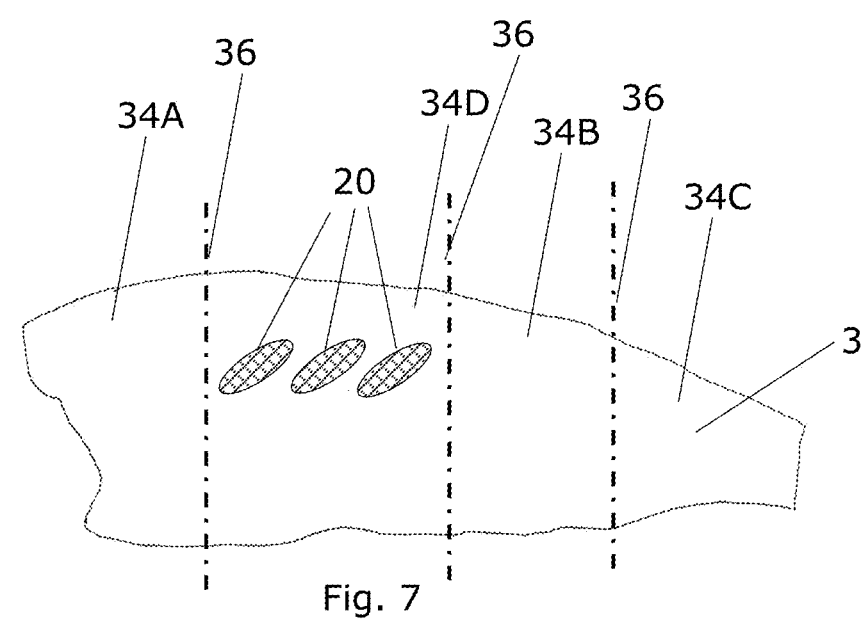
FIG. 7 illustrates the result of a method comprising determining a distribution of fish fillet item portion cuts.

FIG. 7 illustrates the result of a method comprising:
determining one or more positions of one or more candidate gaping areas of the fish fillet item on the basis of at least the
  i. three-dimensional profile data of the fish fillet item; and
  ii. optical imaging data, such as wherein the optical imaging data being colour imaging data of the fish fillet item;
determining a distribution 36 of fish fillet item portion cuts over the fish fillet item dividing the fish fillet item into fish fillet item portions on the basis of at least the determined one or more positions of the one or more candidate gaping areas and at least one fish portion feature, such as portion weight or minimum portion weight.

By cutting the fish item along dash-dotted line 36 the result is three pieces 34A-C without gaping areas, and only one piece 34D with gaping areas. Thus, the three pieces 34A-C have high value and are applicable for a wide range of purposes, even if the original fish fillet item had a low value due to gaping and little or no applicability. A less intelligent cutting could have resulted in, e.g., a single cut through the gaping areas, which would result in both the resulting cut portions having gaping areas.

Figure 8:
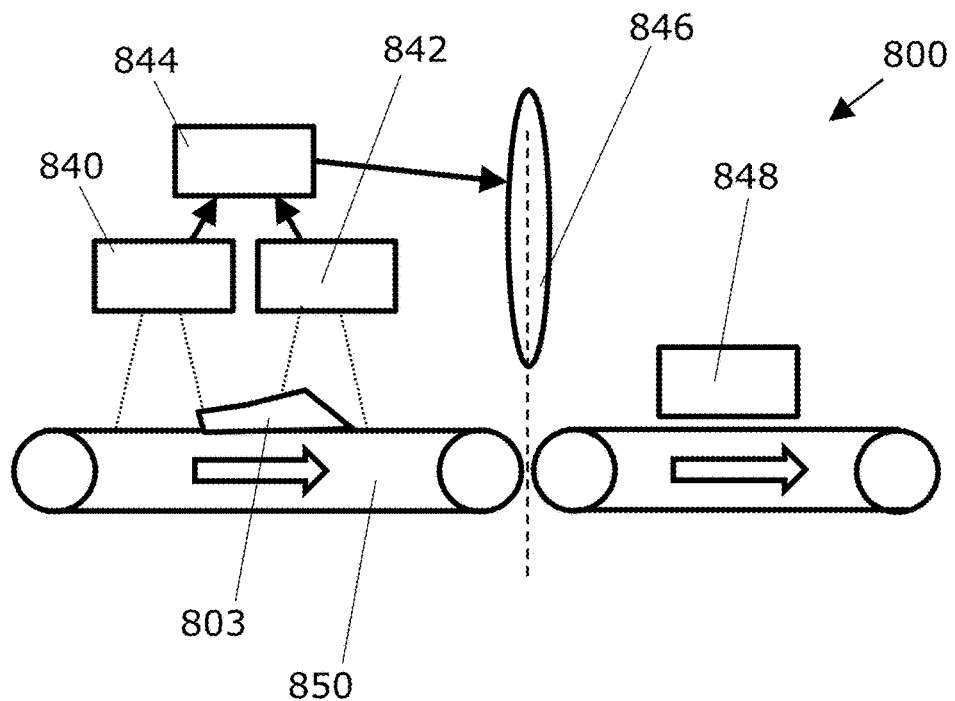
FIG. 8 shows a fish fillet item processing apparatus.

FIG. 8 shows a fish fillet item processing apparatus 800 for determining a measure of gaping in a fish fillet item comprising:
  a three-dimensional profile determining device 840, such as a camera and a line laser, for generating three-dimensional profile data of a first area of the fish fillet item;
  an optical imaging device 842, such as a camera (which could in other embodiments be the same camera as the camera in a three-dimensional profile determining device 840, for generating optical imaging data of a second area of the fish fillet item, wherein the second area is at least partially overlapping with the first area;
  a processing unit 844, such as a computer, operatively coupled to the three-dimensional profile determining device and the optical imaging device and arranged for carrying out the method according to the first aspect.

The fish fillet item processing apparatus in FIG. 8 furthermore comprises a conveyor 850 for conveying a fish item 803 from left to right as indicated by the non-filled arrows, a cutting apparatus 846 receiving a cutting distribution from the processing unit 844 as indicated by the arrow between processing unit 844 and cutting apparatus 846. The fish fillet item processing apparatus in FIG. 8 furthermore comprises a sorting unit 848 receiving information from the processing unit 844 (not shown).

The processing unit may be operatively connected to a storage device comprising a computer program, such as a computer program product, comprising instructions which, when the program is executed by a computer, cause the computer to carry out the method of according to the first aspect.

The fish item processing apparatus may be arranged for carrying out an automated and inline method for determining a measure of gaping in a fish fillet item (and for cutting, such as cutting the fish fillet item into fish fillet item portions according to a determined distribution of fish fillet item portion cuts, and for sorting).

Figure 9:
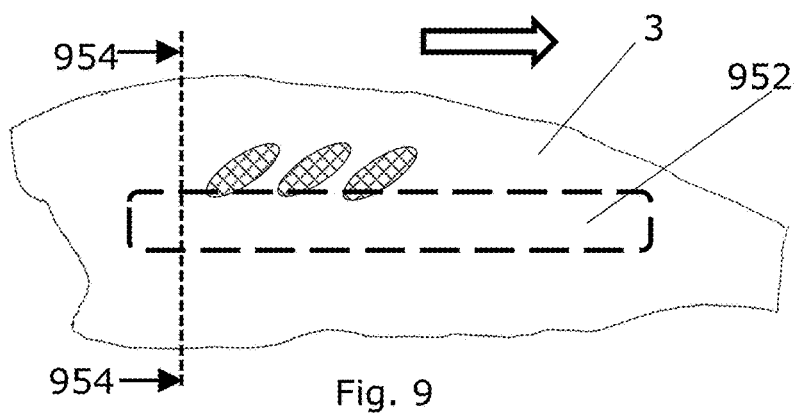
FIG. 9-10 shows a method wherein during obtaining the three-dimensional profile data; and/or the optical imaging data at least a part of the fish fillet item is placed on a non-planar surface.
Figure 10:
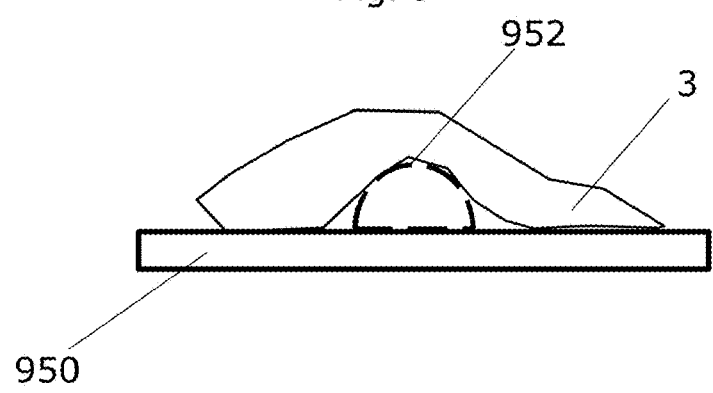

FIG. 9-10 shows a method wherein during obtaining
  The three-dimensional profile data; and/or
  The optical imaging data;
at least a part of the fish fillet item is placed on a non-planar surface (952).

FIG. 9 shows a top view of a fish fillet item 3 during said obtaining (one or both types of data) where the plane of the paper is horizontal, and the viewing direction is vertical. The figure also indicates a non-planar surface 952 upon which the fish fillet item is placed. The fish fillet item is in the figure placed on a conveyor belt with conveying direction from left to right, as indicated by the non-filled arrow, which is parallel with a spine direction of the fish fillet item. Section 954 is depicted in FIG. 10.

FIG. 10 shows the cross-sectional view 954 (as indicated in FIG. 9) of a fish fillet item 3 during said obtaining (one or both types of data) where the plane of the paper is horizontally aligned. The figure also indicates a non-planar surface 952, such as the surface of an elongated convex feature placed on an otherwise flat conveyor belt 950, upon which the fish fillet item is placed.

The non-planar surface comprises an elongated convex feature arranged so that at least a portion of the fish fillet item is bent around an axis being substantially parallel with a direction of a spine (if the spine would still have been present), which direction in FIG. 9 is left-right horizontal and in FIG. 10 is orthogonal to the plane of the paper, during measuring the three-dimensional profile data and/or the optical imaging data. The fish fillet item is conveyed in a direction (cf., the non-filled arrow in FIG. 9) substantially parallel with a direction of a spine and an elongated and oriented in a direction substantially parallel with the conveying direction convex feature of the conveyor is placed so as to substantially coincide with a fat centreline (cf., e.g., the thick dashed line in FIG. 6 which is left out for clarity in FIGS. 9-10) of the fish fillet item during obtaining, such as measuring, the three-dimensional profile data and/or the optical imaging data.

Figure 11:
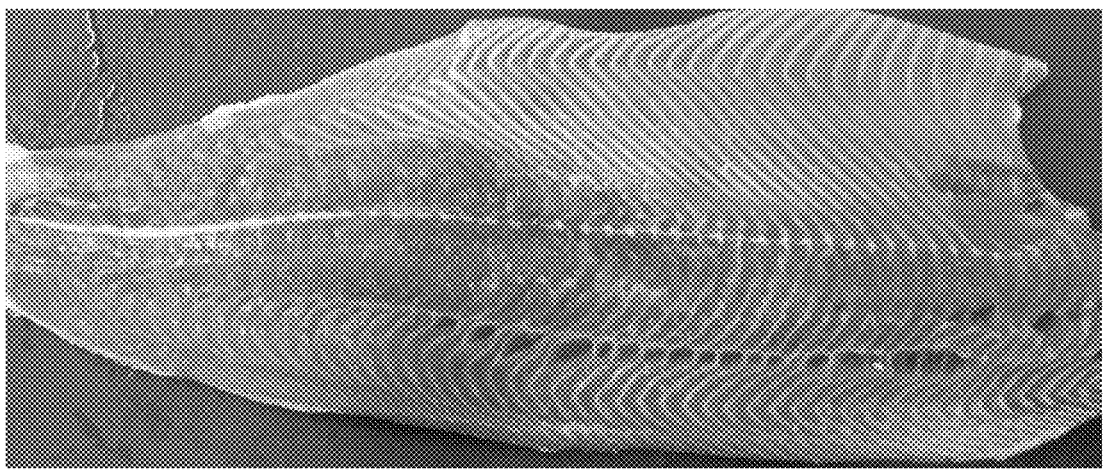
FIGS. 11-13 show examples of fish fillets with gaping which could be according to categories 2-4.
Figure 12:
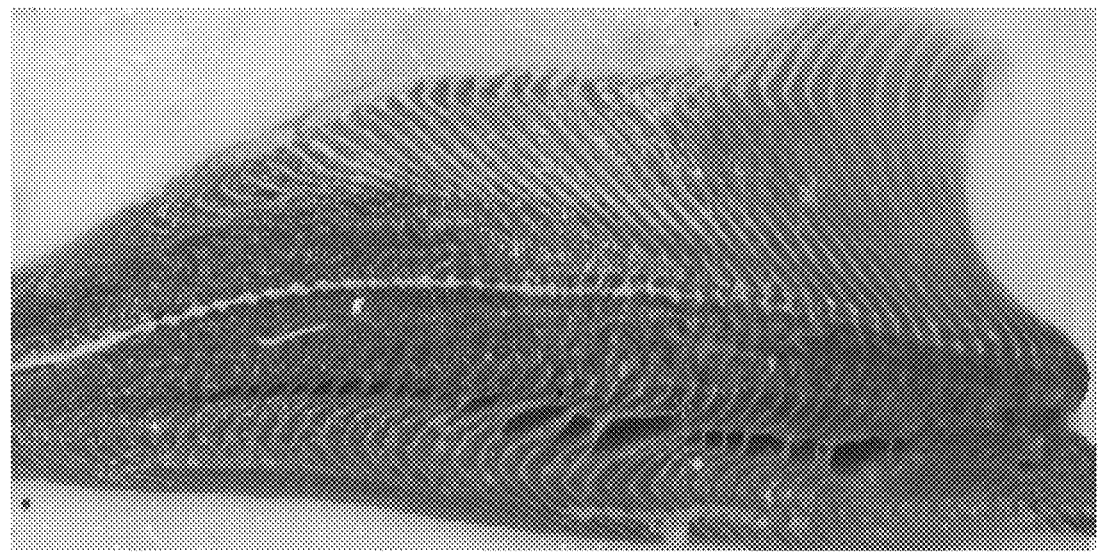
Figure 13:
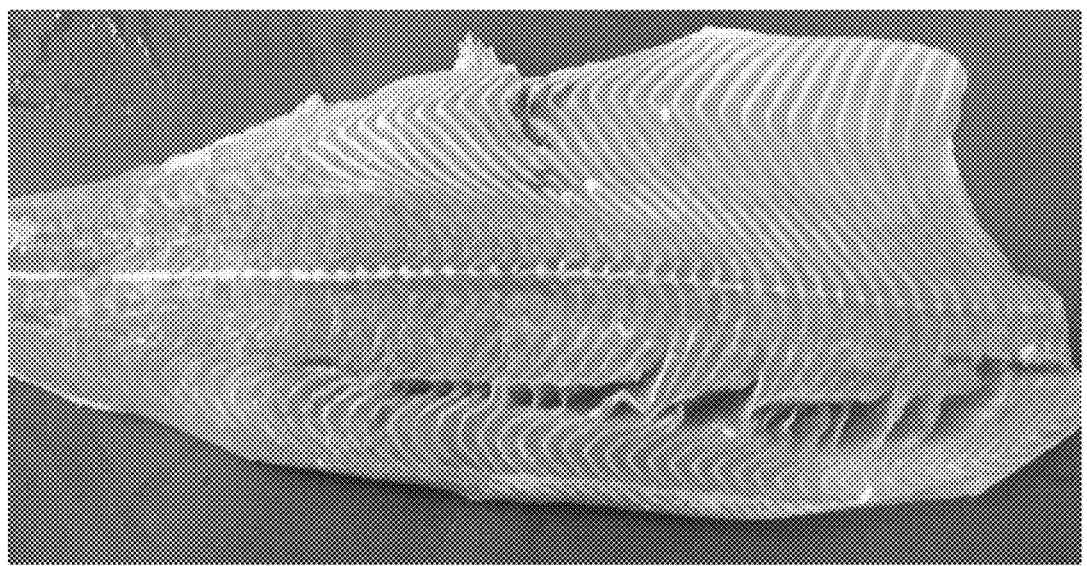

FIG. 11-13 show examples of fish fillets with gaping which could be according to (the previously mentioned) categories 2-4.

FIG. 11 shows a fish fillet which could be classified into gaping category 2.

FIG. 12 shows a fish fillet which could be classified into gaping category 3.

FIG. 13 shows a fish fillet which could be classified into gaping category 4.

FIGS. 14-17 show three-dimensional profile data and optical imaging data for a first fish fillet example.

Figure 14:
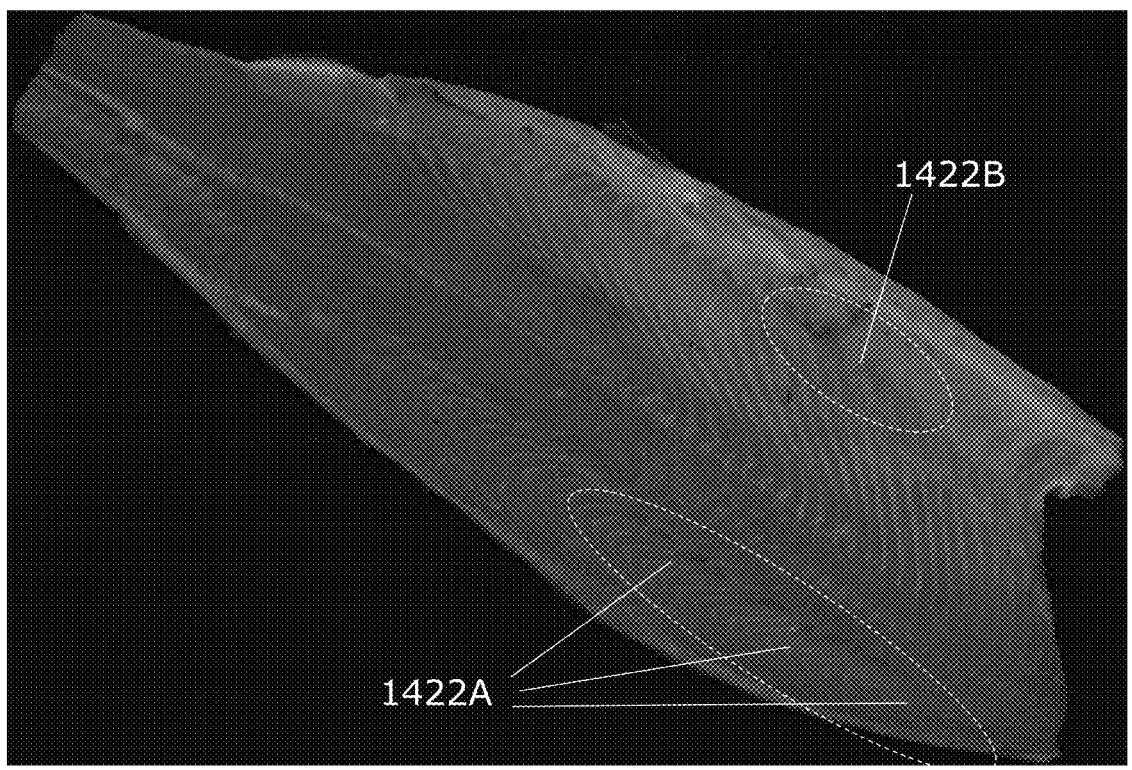
FIGS. 14-17 show 3D profile data and optical imaging data for a first fish fillet example.

FIG. 14 shows optical image data in the form of a digital colour image (which in the present representation, however, is converted to grey tones) of the first fish fillet example. FIG. 14 shows that a candidate gaping area set based on the optical imaging data could correctly comprise gaping areas 1422A (because they can be seen in the optical image data). However, a false positive gaping area 1422B could also be included (because it could be interpreted based on the optical image data alone to be a gaping area due to the darker colour reminiscent of the colour of gaping areas, but where the darker colour in the optical image data is in fact due to a discoloration of the fish fillet item rather than topographical gaping-features).

Figure 15:
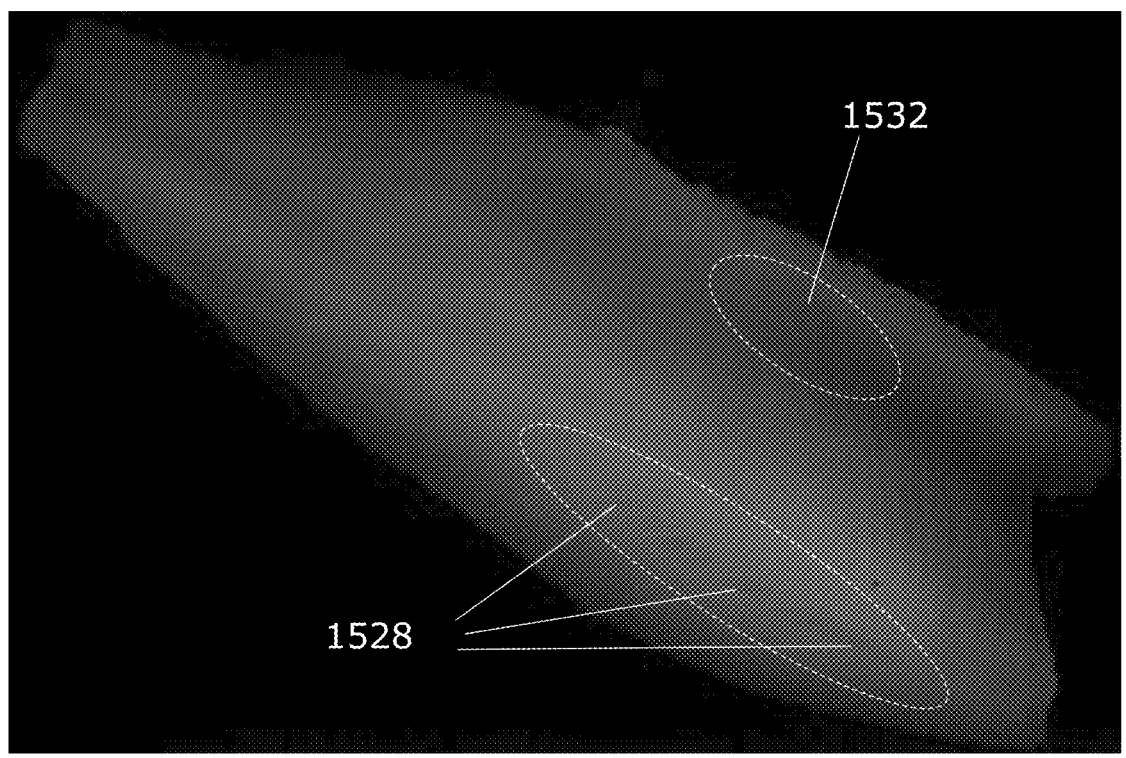

FIG. 15 shows three-dimensional image data of the first fish fillet example visualized via a grey scale representation. FIG. 15 shows that a candidate gaping area set based on the three-dimensional profile data could correctly comprise gaping areas 1528 (corresponding to gaping areas 1422A in FIG. 14) because they can be seen in the three-dimensional image data. Furthermore, the figure shows an area 1532 where no gaping is present, which enables ruling out that the (discoloration-)area 1422B in FIG. 14 is representative of a gaping area.

Figure 16:
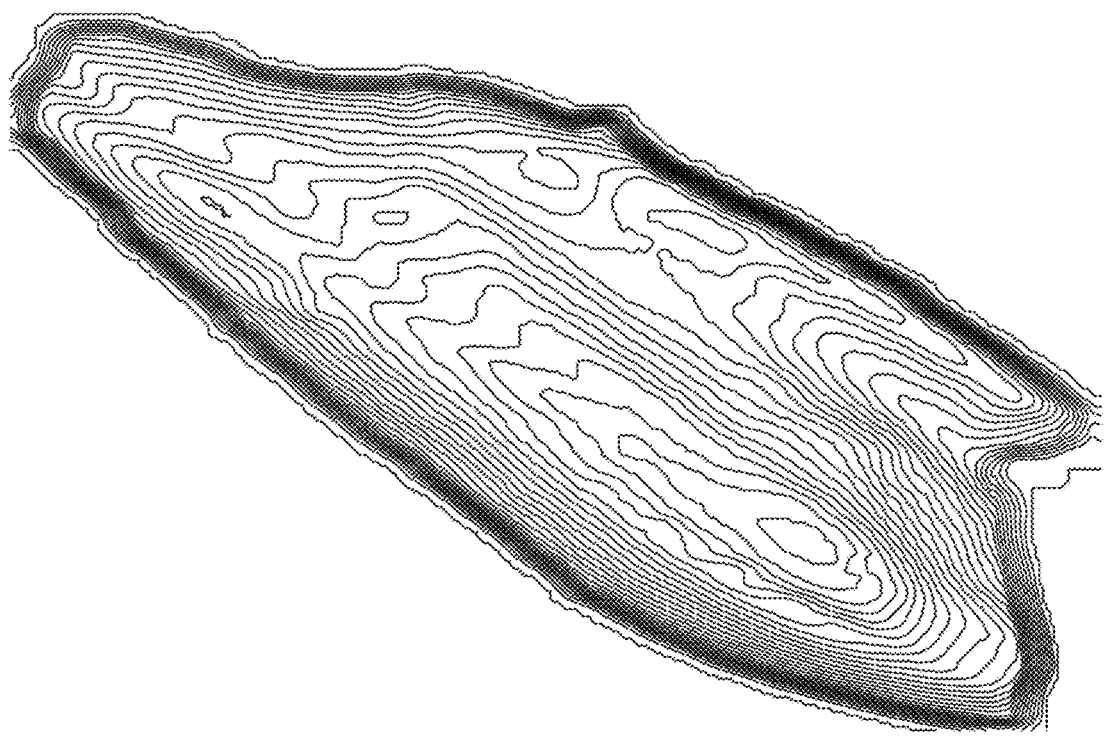

FIG. 16 shows three-dimensional image data of the first fish fillet example (identical to the three-dimensional image data of FIG. 15) visualized via a contour line representation.

Figure 17:
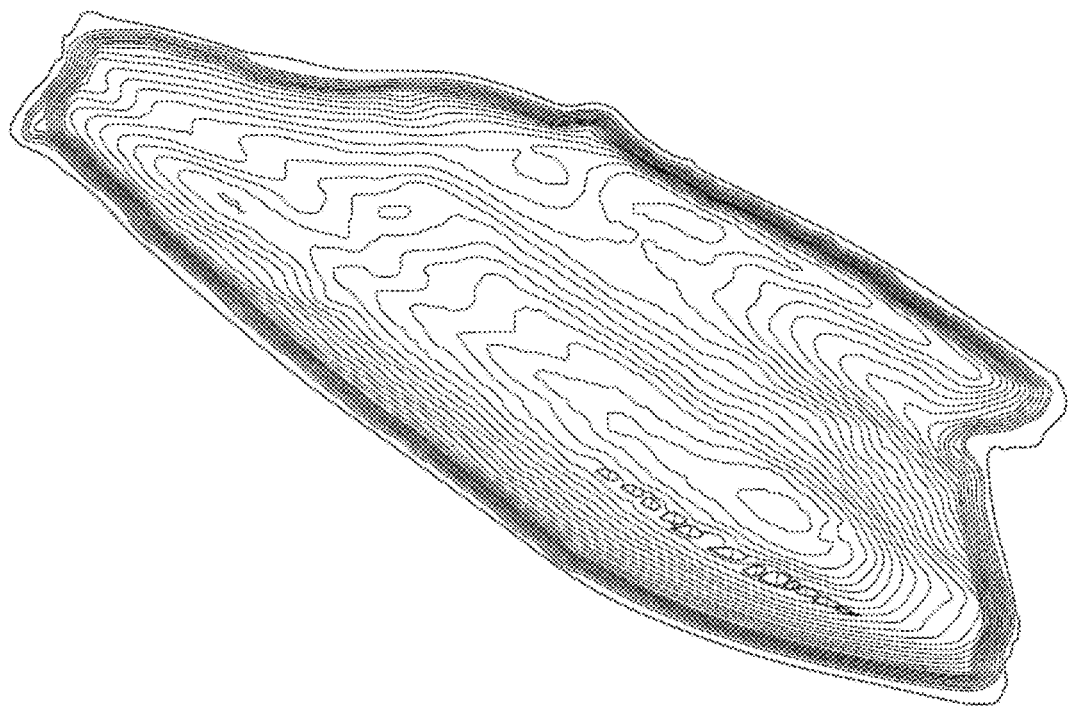

FIG. 17 shows a contour line height map of the first fish fillet example identical to FIG. 16, except that gaping areas have been indicated by a full-drawn, thick line on the border of the gaping areas and a line through the middle of them.

FIGS. 18-21 show a set of three-dimensional profile data and optical imaging data for a second fillet example.

Figure 18:
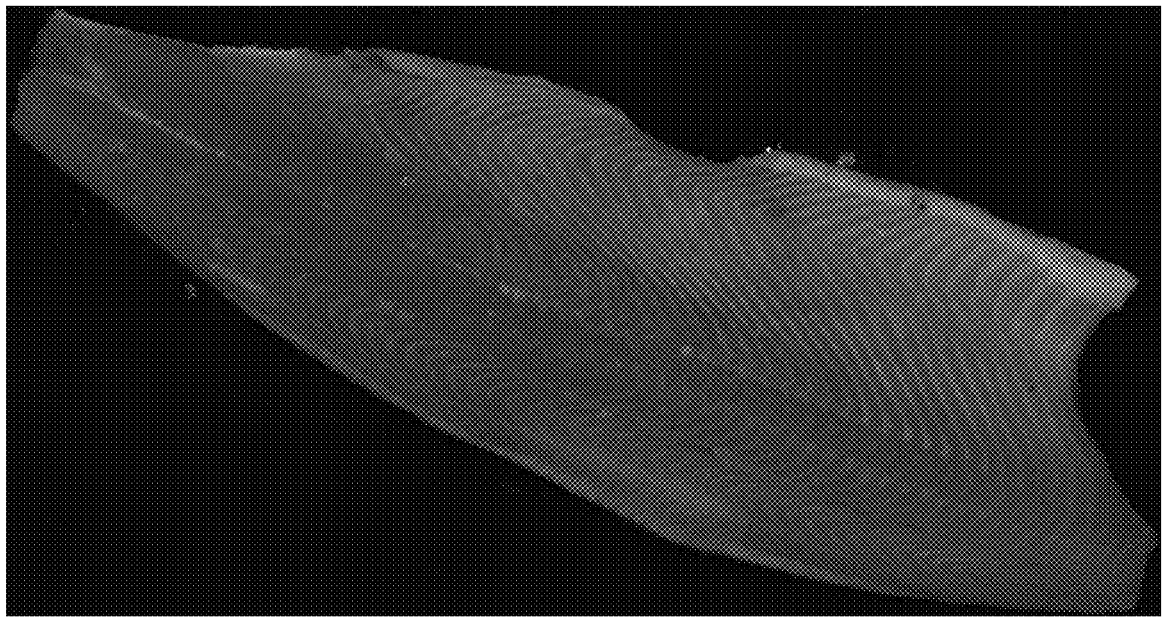
FIGS. 18-21 show 3D profile data and optical imaging data for a second fillet example.

FIG. 18 shows optical image data in the form of a digital colour image (which in the present representation, however, is converted to grey tones) of the second fish fillet example.

Figure 19:
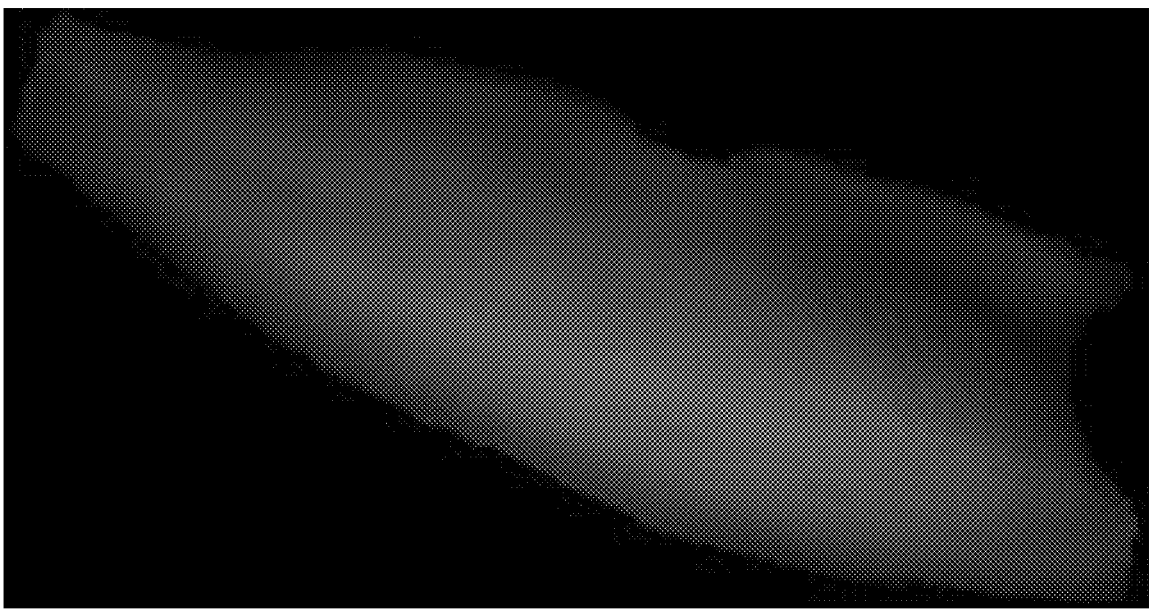

FIG. 19 shows three-dimensional image data of the first second fillet example visualized via a grey scale representation.

Figure 20:
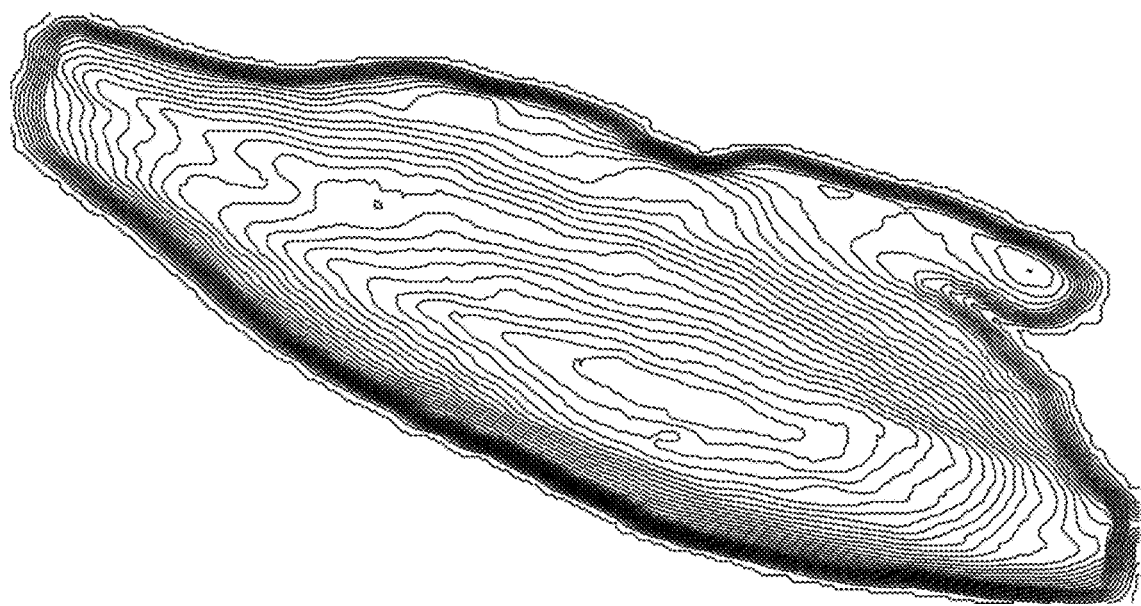

FIG. 20 shows three-dimensional image data of the second fish fillet example (identical to the three-dimensional image data of FIG. 19) visualized via a contour line representation.

Figure 21:
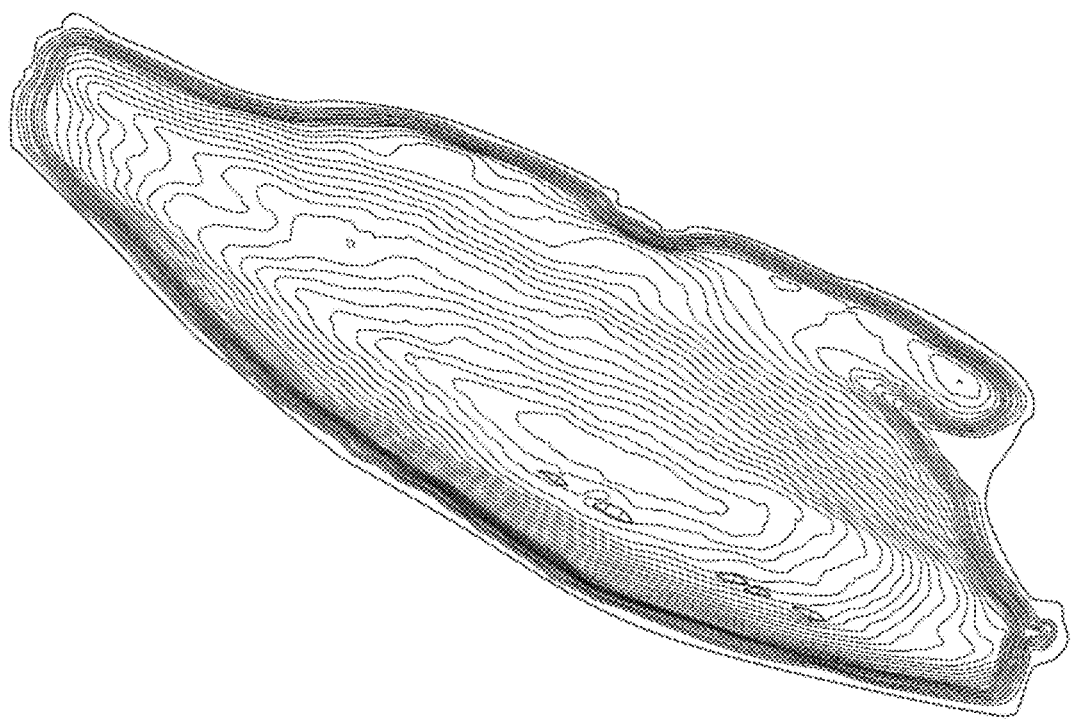

FIG. 21 shows a contour line height map of the second fish fillet example identical to FIG. 20, except that gaping areas have been indicated by a full-drawn, thick line on the border of the gaping areas and a line through the middle of them.

FIGS. 22-25 show a set of three-dimensional profile data and optical imaging data for a third fish fillet example.

Figure 22:
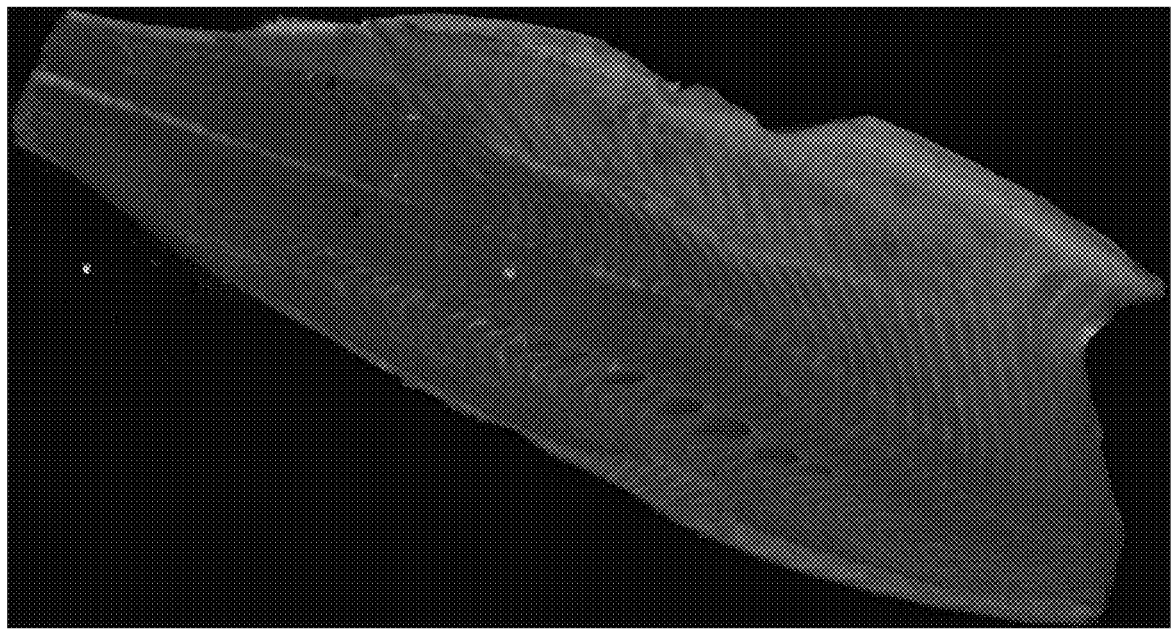
FIGS. 22-25 show 3D profile data and optical imaging data for a third fish fillet example.

FIG. 22 shows optical image data in the form of a digital colour image (which in the present representation, however, is converted to grey tones) of the third fish fillet example.

Figure 23:
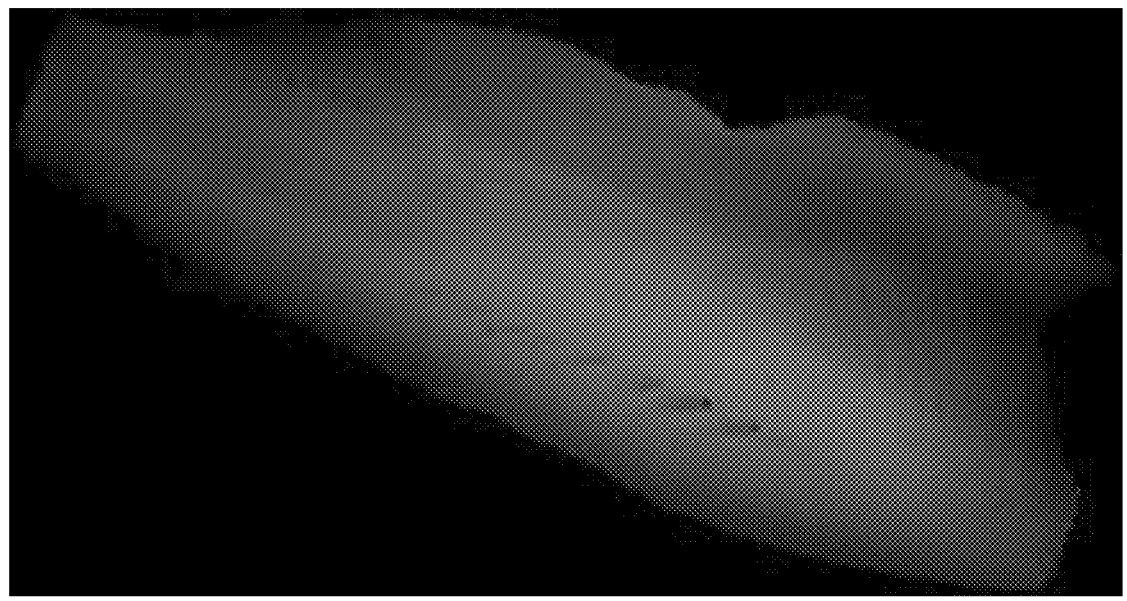

FIG. 23 shows three-dimensional image data of the third fish fillet example visualized via a grey scale representation.

Figure 24:
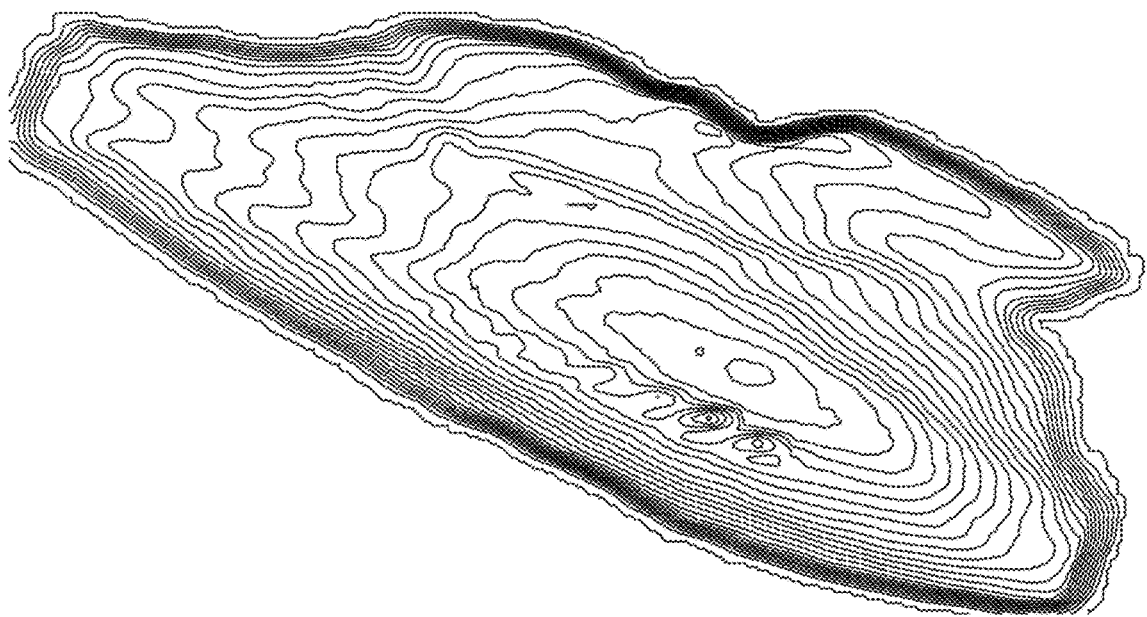

FIG. 24 shows three-dimensional image data of the third fish fillet example (identical to the three-dimensional image data of FIG. 23) visualized via a contour line representation.

Figure 25:
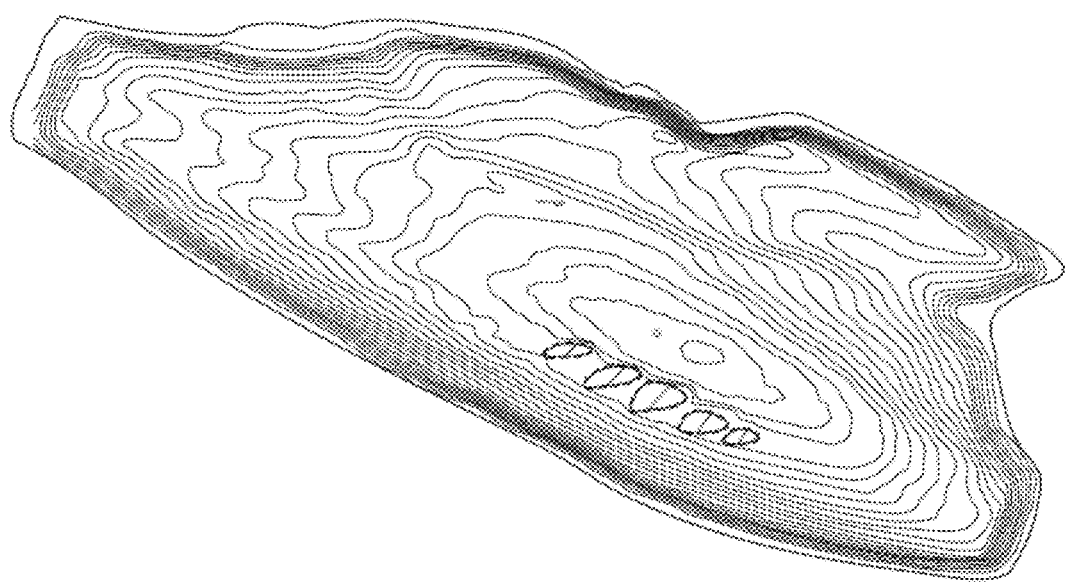

FIG. 25 shows a contour line height map of the third fish fillet example identical to FIG. 24, except that gaping areas have been indicated by a full-drawn, thick line on the border of the gaping areas and a line through the middle of them.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A method of determining a measure of gaping in a fish fillet item, the method comprising the steps of:
    obtaining three-dimensional profile data of a first area of the fish fillet item;
    obtaining optical imaging data of a second area of the fish fillet item, wherein the first area and the second area are overlapping at least within an overlap area;
    determining a measure of gaping in the fish fillet item based on the
    (i) three-dimensional profile data within the overlap area, and the
    (ii) optical imaging data within the overlap area.

2. The method of determining a measure of gaping in a fish fillet item according to claim 1, wherein the method comprises the step of:
    determining a candidate gaping area set based on the
    (i) three-dimensional profile data of the fish fillet item; and/or the
    (ii) optical imaging data of the fish fillet item; and
    wherein determining the measure of gaping in the fish fillet item is based on the candidate gaping area set.

3. A method of determining a measure of gaping in a fish fillet item, the method comprising the steps of:
    obtaining optical imaging data of a second area of the fish fillet item, wherein the first area and the second area are overlapping at least within an overlap area;
    determining a measure of gaping in the fish fillet item based on the
    (i) three-dimensional profile data within the overlap area, and the
    (ii) optical imaging data within the overlap area;
    obtaining three-dimensional profile data of a first area of the fish fillet item;

wherein determining the measure of gaping in the fish fillet item comprises determining a candidate gaping area set of the fish fillet item, in which each candidate gaping area passes each of:
a test where pass or failure is based on the three-dimensional profile data, based exclusively on the three-dimensional profile data, of the fish fillet item; and
a test where pass or failure is based on the optical imaging data, based exclusively on the optical imaging data, of the fish fillet item.

4. The method of determining a measure of gaping in a fish fillet item according to claim 3, wherein the test where pass or failure is based on the optical imaging data of the fish fillet item comprises comparing an actual value of the optical imaging data of the fish fillet item in a position in or adjacent to the candidate gaping area with one or more expected values of the optical imaging data of the fish fillet item in the position in or adjacent to the candidate gaping area.

5. The method of determining a measure of gaping in a fish fillet item according to claim 3, wherein the test where pass or failure is based on the optical imaging data of the fish fillet item comprises comparing an actual value of the optical imaging data of the fish fillet item in a position adjacent to the candidate gaping area, with one or more expected values of the optical imaging data of the fish fillet item in the position adjacent to the candidate gaping area.

6. The method of determining a measure of gaping in a fish fillet item according to claim 3, wherein the test where pass or failure is based on the three-dimensional profile data of the fish fillet item comprises comparing an actual value of the three-dimensional profile data of the fish fillet item in a position adjacent to the candidate gaping area, with one or more expected values of the three-dimensional profile data of the fish fillet item in the position adjacent to the candidate gaping area.

7. The method of determining a measure of gaping in a fish fillet item according to claim 3, wherein determining the measure of gaping in the fish fillet item is based on the candidate gaping area set.

8. The method of determining a measure of gaping in a fish fillet item according to claim 1, arranged for allowing, at least under certain circumstances, depending on the optical imaging data, that an area of the fish fillet item contributes to the measure of gaping even if it is not considered a gaping area based on the three-dimensional profile data.

9. The method of determining a measure of gaping in a fish fillet item according to claim 1, arranged for allowing, at least under certain circumstances, depending on the optical imaging data, that an area of the fish fillet item does not contribute to the measure of gaping even if it is considered a gaping area based on the three-dimensional profile data.

10. The method of determining a measure of gaping in a fish fillet item according to claim 1, arranged for allowing, at least under certain circumstances, depending on the three-dimensional profile data, that an area of the fish fillet item contributes to the measure of gaping even it is not considered a gaping area based on the optical imaging data.

11. The method of determining a measure of gaping in a fish fillet item according to claim 1, arranged for allowing, at least under certain circumstances, depending on the three-dimensional profile data, that an area of the fish fillet item does not contribute to the measure of gaping even it is considered a gaping area based on the optical imaging data.

12. The method of determining a measure of gaping in a fish fillet item according to claim 1,
wherein the measure of gaping is representative of an amount or degree of gaping, and/or
wherein the measure of gaping is qualified or quantified on a one-dimensional scale, exclusively on a one-dimensional scale.

13. The method of determining a measure of gaping in a fish fillet item according to claim 1, wherein determining the measure of gaping in the fish fillet item comprises simultaneously employing the
(i) three-dimensional profile data within the overlap area, and the
(ii) optical imaging data within the overlap area.

14. The method of determining a measure of gaping in a fish fillet item according to claim 1, wherein the method comprises obtaining:
the three-dimensional profile data; and/or
the optical imaging data;
while at least a part of the fish fillet item is placed on a non-planar surface.

15. The method of determining a measure of gaping in a fish fillet item according to claim 14, wherein the non-planar surface, a conveyor, upon which the fish fillet item, comprises a protrusion having a point being at least 0.5 cm, away from a straight line connecting points on the surface on either side of the protrusion and being within 1 cm to 100 cm from each other.

16. The method of determining a measure of gaping in a fish fillet item according to claim 14, wherein the fish fillet item is placed on a protrusion, which protrusion is elongated, having an aspect ratio being higher than 1, and
wherein a smallest angle between a longitudinal axis of the protrusion and an axis of the fish fillet item parallel with a centreline and/or a backbone of the fish had it been present is equal to or smaller than 60°.

17. The method of determining a measure of gaping in a fish fillet item according to claim 1, wherein the method is an automated and/or inline method.

18. The method of determining a measure of gaping in a fish fillet item according to claim 1, wherein said fish fillet item originates from a fish within the order of salmoniformes, is an item of any one of trout and salmon.

19. The method of determining a measure of gaping in a fish fillet item according to claim 1, wherein determining the measure of gaping in the fish fillet item comprises determining a candidate gaping area set of the fish fillet item, wherein:
in a step A, determining a candidate gaping area set of the fish fillet item based on at least the three-dimensional profile data of the fish fillet item;
in a step B,
(i) subjecting each candidate gaping area to a test where pass or failure is based on the optical imaging data of the fish fillet item; and
(ii) removing from the set any candidate gaping area failing the test.

20. The method of determining a measure of gaping in a fish fillet item according to claim 1, wherein the method further comprises:
determining one or more positions of one or more candidate gaping areas of the fish fillet item on the basis of at least the
(i) three-dimensional profile data of the fish fillet item; and the
(ii) optical imaging data of the fish fillet item.

21. The method of determining a measure of gaping in a fish fillet item according to claim 20, wherein the method further comprises determining a distribution of fish fillet item portion cuts over the fish fillet item dividing the fish fillet item into fish fillet item portions on the basis of at least the determined one or more positions of the one or more candidate gaping areas and at least one fish portion feature.

22. The method of determining a measure of gaping in a fish fillet item according to claim 21, wherein the method further comprises cutting the fish fillet item into fish fillet item portions according to the determined distribution of fish fillet item portion cuts.

23. The method of determining a measure of gaping in a fish fillet item according to claim 1, wherein the method further comprises providing a parameter based on the measure of gaping to an upstream station and/or to a downstream station, including adjusting processing at an upstream station and/or at a downstream station based on said parameter.

24. A fish fillet item processing apparatus for determining a measure of gaping in a fish fillet item comprising:
- a three-dimensional profile determining device, including a camera and a line laser, for generating three-dimensional profile data of a first area of the fish fillet item;
- an optical imaging device, including a camera, for generating optical imaging data of a second area of the fish fillet item, wherein the second area is at least partially overlapping with the first area; and
- a processing unit, including a computer, operatively coupled to the three-dimensional profile determining device and the optical imaging device.

25. A non-transitory computer readable medium storing a computer program, comprising instructions which, when the program is executed by a computer, cause the computer to carry out a method comprising the steps of:
- obtaining three-dimensional profile data of a first area of a fish fillet item;
- obtaining optical imaging data of a second area of the fish fillet item, wherein the first area and the second area are overlapping at least within an overlap area;
- determining a measure of gaping in the fish fillet item based on the
  - (i) three-dimensional profile data within the overlap area, and the
  - (ii) optical imaging data within the overlap area,
- and/or comprising instructions to cause a fish fillet item processing apparatus for determining a measure of gaping in a fish fillet item comprising:
- a three-dimensional profile determining device, including a camera and a line laser, for generating three-dimensional profile data of a first area of the fish fillet item;
- an optical imaging device, including a camera, for generating optical imaging data of a second area of the fish fillet item, wherein the second area is at least partially overlapping with the first area; and
- a processing unit, including a computer, operatively coupled to the three-dimensional profile determining device and the optical imaging device;
- wherein said apparatus is arranged to execute the steps of said method.

* * * * *